United States Patent [19]

Shen et al.

[11] Patent Number: 5,254,342
[45] Date of Patent: Oct. 19, 1993

[54] COMPOSITIONS AND METHODS FOR ENHANCED TRANSEPITHELIAL AND TRANSENDOTHELIAL TRANSPORT OR ACTIVE AGENTS

[75] Inventors: Wei-Chiang Shen, San Marino; Jiansheng Wan, Montery Park, both of Calif.

[73] Assignee: University of Southern California, Los Angeles, Calif.

[21] Appl. No.: 768,508

[22] Filed: Sep. 30, 1991

[51] Int. Cl.[5] .......................... C12N 5/02; C12N 5/06; C12N 5/08
[52] U.S. Cl. .................................. 424/401; 424/447; 435/240.1; 435/240.2; 435/240.3; 435/240.31
[58] Field of Search ........................... 424/401, 447; 435/240.1, 240.2, 240.3, 240.31

[56] References Cited

U.S. PATENT DOCUMENTS 5,108,921  4/1992  Lowe et al. ............... 435/243

OTHER PUBLICATIONS

Artursson, P., "Epithelial Transport of Drugs in Cell Culture", *J. Pharm. Sci.* 79:476–482 (1990).
Balch, W. E., "Biochemistry of Interorganelle Transport", *J. Biol. Chem.* 264:16956–16968 (1989).
Banerjee, D. Flanagan et al., "Transferrin Receptors in the Human Gastrointestinal Tract: Relationship to Body Iron Stores", *Gastroenterology* 91:861–869 (1986).
Breitfeld, P. P. et al., "Sorting Signals, Current Opinion", *Cell Biol.* 1:617–623 (1989).
Chantret, I. et al., "Epithelial Polarity, Villin Expression, and Enterocytic Differentiation of Cultured Human Colon Carcinoma Cells: A survey of Twenty Cell Lines", *Cancer Research* 48:1936–1942 (1988).
Cho, M. J. et al., "The Madin Carby Canine Kidney (MDCK) Epithelial Cell Monolayer as a Model Cellular Transport Barrier", *Pharm. Research.* 6, No. 1.
Dautry-varsat, A. et al., "pH and the Recycling of Transferring During Receptor Mediated Endocytosis", *Proc. Natl. Acad. Sci. USA* 80:2258–2262 (1983).
Davis, C. G. et al., "The Low Density Lipoprotein Receptor", *J. Biol. Chem.* 262:4075 (1987).
DeDuve, C., "Lysosomes Revisited", *Eur. J. Biochem.*, 137:391–397 (1983).
Farquhar, M. G., "Recovery of Surface Membrane in Anterior Pituitary Cells. Variations in Traffic Detected with Anionic and Cationic Ferritin", *J. Cell Biol.* 77:/R35-42 (1978).
Farquhar, M. G. "Membrane Recycling in Secretory Cells: Implications For Traffic of Products and Specialized Membranes Within the Golgi Complex", *Cell. Biol.* 23:399–427 (1981).
Fishman, J. B. et al., "Receptor-Mediated Transcytosis of Transferring Across the Blood Brain Barrier", *J. Neuroscience Res.* 18:299–304 (1987).

(List continued on next page.)

Attorney, Agent, or Firm—Robbins, Berliner & Carson

[57] ABSTRACT

Compositions and methods for use in enhancement of transmembrane and transcellular transport of an active agent, in particular a peptide or protein, in which at least one carrier for transmembrane or transcellular transport of an active agent which is a ligand for a cell-surface receptor is used to form a ligand/active agent conjugate and at least one transfer enhancement agent which enhances transcytosis of the resultant cell-surface receptor/ligand complex is administered to accelerate transcytosis. As an example, the effects of brefeldin A and monensin on transferrin (Tf) transcellular transport, Tf receptor (TfR) distribution and TfR-mediated endocytosis in filter-grown MDCK cells are described. The transfer enhancement agents markedly enhanced the transcytosis of ligand/active agent complexes in both the apical-to-basal and the basal-to-apical directions, but did not increase the transcytosis of agents which were not bound to a cell-surface receptor ligand as carrier. Furthermore, this enhanced transcytosis was abolished by competition with excess unlabeled Tf, confirming that it was a TfR-mediated process.

2 Claims, 6 Drawing Sheets

Fishman, J. B. and Fine, R. E., "A Trans Golgi-Derived Exocytic Coated Vesicle Can Contain Both Newly Synthesized Cholinesterase and Inernalized Transferrin", *Cell* 48:157–164 (1987).

Friden, P. M. et al., "Anti-transferrin Receptor Antibody and Antibody-drug Conjugates Cross the Blood-brain Barrier", *Proc. Natl. Acad. Sci USA* 88:4771–4775 (1991).

Fujiwara, T. et al., "Brefeldin A Causes Disassembly of the Golgi Complex and Accumulation of Secretory Protein in the Endoplasmic Reticulum", *J. Biol. Chem.* 263:18545–18552.

Fuller, S. D., and Simons, K., "Transferrin Receptor Polarity and Recycling Accuracy in Tight and Leaky Strains of Madin-Darby Canine Kidney Cells", *J. Cell. Biol.* 103:1767–1779 (1986).

Ghitescu, L. et al., "Specific Binding Sites for Albumin Restricted to Plasmalemmal Vesicles of Continuous Capillary Endothelium: Receptor-mediated Transcytosis", *J. Cell. Biol.* 102:1304–1311 (1986).

Glenney, J. R. et al., *Cell* 52:675 (1988).

Goldberg, D. E. and Kornfeld, S., "Evidence for Extensive Subcellular Organization of Asparagine-linked Oligasaccharide Processing and Lysosomal Enzyme Phosphorylation", *J. Biol. Chem.* 258:3159–3165 (1983).

Gonzalez-Mariscal, L., "Tight Junction Formation in Cultured Epithelial Cells (MDCK)", *J. Membr. Biol.* 86:113–125 (1985).

Grasset, E. et al., "Epithelial Properties of Human Colonic Carcinoma Cell Line Caco-2: Electrical Parameters", *Am. J. Physiol.* 247:C2560–C267 (1984).

Herzog, V. and Farquhar, M. G., "Luminal Membrane Retrieved After Exocytosis Reaches Most Golgi Chisternea in Secretory Cells", *Proc. Natl. Acad. Sci. USA* 74:5073–5077 (1977).

Heyman, M. et al., "Quantification of Protein Transcytosis in the Human Colon Carcinoma Cell Line Ca-Co-2", *J. Cell Physiol.* 143:391–395 (1990).

Hidalgo, I. J. et al., "Characterization of the Human Colon Carcinoma Cell Line (Caco-2) As a Model System for Intestinal Epithelial Permeability", *Gastroenterology* 96:736–749 (1989).

Jeffries, A. E. et al., "Transferrin Receptor of Endothelium of Brain Capillaries", *Nature* 312:162–163 (1984).

Kato, S. et al., "Effects of Brefeldin A on the Synthesis and Secretion of Egg White Proteins in Primary Cultured Oviduct Cells of Laying Japanese Quail", *Biochem. Biophy. Acta* 991:36–43 (1989).

King, G. L. and Johnson, S. M., "Receptor-Mediated Transport of Insulin Across Endothelial Cells", *Science* 227:1583–1586 (1985).

Klausner, R. D. et al., "Binding of Apotransferrin to K562 Cells; Explanation of the Transferrin Cycle", *Proc. Natl. Acad. Sci. USA* 80:2263–2266 (1983).

Klausner, R. D. et al., "Failure to Release Iron from Transferrin in a Chinese Hamster Ovary Cell Mutant Pleiotropically Defective in Endocytosis", *J. Cell Biol.* 98:1098–1101 (1984).

Larrick, J. and Cresswell, P., "Transferrin Receptors on Human B and T Lymphoblastoid Cell Lines", *Biochem. Biophys. Acta* 583:483–490 (1979).

Lippincott-Schwartz, J. et al., "Rapid Redistribution of Golgi Proteins into the ER in Cells Treated with Brefeldin A: Evidence for Membrane Cycling from Golgi to ER", *Cell* 56:801–813 (1989).

Lippincott-Schwartz, J. et al., "Rapid Redistribution of Golgi Proteins into the ER in Cells Treated with Brefeldin A: Evidence for Membrane Cycling from Golgi to ER", *Cell* 60:821–836 (1990).

Magner, J. A. and Papagianner, E., "Blockade by Brefeldin A of Intracellular Transport of Secretory Proteins in Mouse Pituitary Cells: Effects on the Biosynthesis of Thyrotropin and Free a-Subunits", *Endocrinology* 122:912–920 (1988).

Maratos-Flier, E. et al., "Receptor-Mediated Vectorial Transcytosis of Epidermal Growth Factor by Madin-Darby Canine Kidney Cells", *J. Cell Biol.* 105:1595–1601 (1987).

Maxfield, F. R., "Weak Bases and Ionophores Rapidly and Reversibly Raise the pH of Endocytic Vesicles in Cultured Mouse Fibroblasts", *J. Cell Biol.* 95:676–681 (1982).

Misumi, Y. et al., "Novel Blockade by Brefeldin A of Intracellular Transport of Secretory Proteins in Cultured Rat Hepatocytes", *J. Biol. Chem.* 261:11398–11403 (1986).

Mollenharer, H. H. et al., "Alteration of Intracellular Traffic by Monensin; Mechanism, Specificity and Relationship to Toxicity", *Biochimica et Biphysica Acta* 1031:225–246 (1990).

Mostov, K. E. and Simister, N.E., "Transcytosis", *Cell* 43:389–390 (1985).

Muranishi, S., "Absorption Enhancers", *CRC Critical Review in Therapeutic Drug Carrier Systems* 7:1–33 (1990).

Neuwelt, E. A. et al., "Delivery of Melanoma-associated Immunoglobulin Monoclonal Antibody and Fab Fragments to Normal Brain Utilizing Osmotic Blood-Brain Barrier Disruption", *Cancer Res.* 48:4725–4729 (1988).

Neuwelt, E. A. et al., "Developments in the Diagnosis and Treatment of Primary CNS Lymphoma", *Cancer* 58:1609–1620 (1986).

Nishihata, T. et al., "Enhanced Intestinal Absorption of Insulin in Rats in Presence of Sodium 5-methoxy salicylate", *Diabetes* 30:1065 (1981).

Oda, K. et al., "Brefeldin A Arrests the Intracellular Transport of a Precursor of Complement C3 Before Its Conversion Site in Rat Hepatocytes", *FEBS Lett.* 214:135–138 (1987).

Orci, L. et al., "Brefeldin A, a Drug that Blocks Secretion, Prevents the Assembly of Non-clthrin-coated Buds on Golgi Cisternae" *Cell* 64:1183–1195 (1991).

Pardridge, W. M. et al., "Human Blood Brain Barrier Transferrin Receptor", *Metabolism* 36:892–895 (1987).

Pardridge, W. M. et al., "β-Endorphin Chimeric Peptides: Transport Through the Blood-Brain Barrier In Vivo and Cleavage of Disulfide Linkage by Brain", *Endocrinol.* 126:977–984 (1990).

Perkel, V. S. et al., "Brefeldin A Inhibits Oligosaccharide Processing of Glycoproteins in Mouse Hypothyroid Pituitary Tissue at Several Subcellular Sites (42682)", *Endocrinology* 123:310–318 (1988).

Pinto, M. et al., "Enterocyte-like Differentiation and Polarization of the Human Colon Carcinoma Cell Line Caco-2 in Culture", *Biol. of the Cell* 47:323–330 (1983).

Pohlmann, R. A. et al., "Synthesis of Phosphorylated Recognition Marker in Lysosomal Enzymes is Located in the cis Part of Golgi Apparatus", *J. Biol. Chem.* 257:5323–5325 (1982).

Princiotto, J. V., "Difference Between the Two Ino--binding Sites of Transferrin", *Nature* 255:87–88 (1975).

Regoeczi, E. et al., "Partial Resialylation of Human Asialotransferrin Types 1 and 2 in the Rat", *Can. J. Biochem. Cell Biol.* 62:852–858 (1984).

Rodewald, R., "Distribution of Immunoglobulin G Receptors in the Small Intestine of the Young Rat", *J. Cell Biol.* 85:18–32 (1980).

Rodman, J. S. et al., "Endocytosis and Transcytosis", Current Opinion in *Cell Biology* 2:644–672 (1989).

Rodriquez-Boulan, E. and Nelson, W. J., "Morphogenesis of the Polarized Epithelial Cell Phenotype", *Science* 245:718–725 (1989).

Rodriquez-Boulan, E. and Salas, P. J. I., "External and Internal Signals for Epithelial Cell Surface Polarization", *Annu. Rev. Physiol.* 51:741–754 (1989).

Shen, W.-C. et al., "Proteolytic Processing in a Non-lysosomal Compartment is Required for Transcytosis of Protein-Polylysine Conjugates in Cultured Madin-Darby Canine Kidney Cells", *Biochem. Biophy. Res. Comm.* 166:316–323 (1990).

Simons, K. and Fuller, S. D., "Cell Surface Polarity in Epithelia", *Annul. Rev. Biol.* 1:243–288 (1985).

Snider, M. D. and Rogers, O. C., "Intracellular Movement of Cell Surface Receptors After Endocytosis: Resialylation of Asialo-Transferrin Receptor in Human Erythroleukemia Cells", *J. Cell Biol.* 100:826–834 (1985).

Stein, B. S. et al., "Complete Inhibition of Transferrin Recycling by Monensin in K562 Cells", *J. Biol. Chem.* 259:14762–14772 (1984).

Stein, B. S. and Sussman, H. H., "Demonstration of Two Distinct Transferrin Receptor Recycling Pathways and Transferrin-independent Receptor Internalization in K562 Cells", *J. Biol. Chem.* 261:10319–10331 (1986).

Takatsuki, A. and Tamura, G., "Brefeldin A, A Specific Inhibitor of Intracellular Translocation of Vesicular Stomatitis Virus G Protein: Intracellular Accumulation of High Mannose Type G Protein and Inhibition of its Cell Surface Expression", *Agric. Biol. Chem.* 49:889–902 (1985).

Tartakoff, A. M., "Perturbation of Vesicular Traffic With the Carboxylic Ionophore Monensin", *Cell* 32:1026–1028 (1983).

Timchak, L. M. et al., "A Thermosensitive Lesion in a Chinese Hamster Cell Mutant Causing Differential Effects on the Acidification of Endosomes and Lysosomes", *J. Biol. Chem.* 261:14154–14159 (1986).

Triguero, D. et al., "Capillary Depletion Method for Quantification of Blood-Brain Barrier Transport of Circulating Peptides and Plasma Proteins", *J. Neurochem* 54:1882–1888 (1990).

Ulmer, J. B. and Palade, G. E., "Effects of Brefeldin A on the Processing of Viral Enveope Glycoproteins in Murine Erythroleukemia Cells", *J. Biol. Chem.* 266:9173–9179 (1991).

Underdown, B. J., "Structural and Functional Aspects of IgA transcytosis", *Immunological Investigations* 18:287–297 (1989).

Wilson, G. et al., "Transport and Permeability Properties of Human Caco-2 Cells: an In Vitro Model of the Intestinal Epithelial Cell Barrier", *J. Controlled Release* 11:25–40 (1990).

*Worthington Enzyme Manual* (1972) Worthington Biochem. Co., Freehold, N.J. pp. 43–45.

*Worthington Manual:* Enzymes Related Biochemicals (1988) pp. 254–260, Worthington Biochem. Co., Freehold, N.J.

Woods, J. W. et al., "Transferrin Receptors Recycle to cis and Middle as Well as Trans Golgi Cisternae in Ig-Secreting Myeloma Cells", *J. Cell Biol.* 103:277–286 (1986).

Yoshida, T. et al., "Disruption of the Golgi Apparatus by Brefeldin A Inhibits the Cytotoxicity of Ricin, Modeccin, and Pseudomonas Toxin", *Experimental Cell Research* 192:389–395 (1991).

Haerri, E. et al., "Uber die Isolierung Neuer Stoffwechselprodukte Aus Penicillinum brefeldianum Dodge", *Helv. Chim. Acta* 46:1235–1243 (1963).

*Primary Examiner*—Thurman K. Page
*Assistant Examiner*—Carlos Azpuru

COMPOSITIONS AND METHODS FOR ENHANCED TRANSEPITHELIAL AND TRANSENDOTHELIAL TRANSPORT OR ACTIVE AGENTS

This invention was made with government support under 5 RO1 CA34798-08 awarded by the National Institute of Health. The government has certain rights in the invention.

BACKGROUND OF THE INVENTION

The present invention relates to methods and compositions for use in the delivery of active agents, such as proteins and peptides, across epithelial and endothelial cell walls.

Many active agents, including most protein and peptide-based drugs, can only be administered via parenteral routes (e.g., intravenous, intramuscular, subcutaneous, intraperitoneal, intraspinal, intrathecal, intracerebroventricular, intraarterial, and other routes of injection). Although these routes of drug delivery remain most effective, especially for patients who suffer from life-threatening diseases, they induce low compliance from patients. There are two primary reasons for this limited compliance. First, many drugs (and in particular, protein and peptide drugs) have very short half lives in vivo, and multiple injections per day are often necessary to maintain effective drug levels in the blood. Second, many patients (especially those who suffer from chronic diseases such as diabetes and other congenital or acquired metabolic disorders) need to take the medicine for their entire lives. It is difficult for these patients to accept a drug therapy regimen which requires daily multiple injections for an extended period of time.

Alternative, non-invasive routes to deliver active agents (i.e., delivery of the drug via oral, nasal, transdermal and other non-parenteral routes) are receiving increasing attention. Non-invasive delivery provides convenience and selfcontrollability. Due to the specific physicochemical properties associated with many active agents (in particular, peptides and proteins), however, most of the active agents of current interest are poorly absorbed when given non-invasively; therefore, when administered in the heretofore-known manner, many of these agents are simply not effective. Although intense research has been carried out in this field in recent years, limited success has been achieved. It remains a great challenge to design and develop an effective and non-invasive delivery system for active agents of current interest, and in particular the peptides and proteins which have become available for potential therapeutic use with the advent of, e.g., recombinant DNA technology. It is envisioned that were an effective delivery system available, the clinical value of peptide- and protein-based pharmaceuticals would be dramatically increased and many patients would benefit accordingly.

Non-invasive routes for drug delivery mainly include the oral, nasal, pulmonary, rectal, buccal, vaginal, transdermal and ocular routes. On the surface of entry to all these routes there exists a continuous mucous membrane of the epithelial cell layer. Before non-invasively delivered drugs can gain access to this epithelial cell monolayer and reach the target situs, there are several obstacles which must be overcome. The active agent must be dissolved and released from the dosage form. Moreover, the drugs must survive the harsh environment of the lumen (e.g., low pH and in the presence of proteolytic and hydrolytic enzymes), and then diffuse across the unstirred microclimate surrounding the epithelium. After reaching the surface of the cell, factors such as residence time at the surface, molecular size, membrane partition coefficient and other physicochemical properties of the drugs, as well as the structural morphology and biological function of the cells, also affect their penetration across the epithelium. Furthermore, during and after transcellular transport, the drugs still face possible enzymatic degradation and immunological and metabolic clearances, such as first-pass clearance in liver. All these factors can potentially block the drug from reaching its final target situs.

Among all of these possible factors, enzymatic degradation and the poor penetration of the drug across epithelial and endothelial cells have been considered to be the major rate limiting steps. The enhancement of macromolecule penetration across epithelial cells is, in particular, a burdensome problem preventing the exploitation of otherwise promising active agents.

The barrier properties of epithelial and endothelial cells exist primarily for two reasons. Adjacent cells are tightly connected by tight junctions which only allow very small water soluble molecules to pass through (paracellular transport). In addition, the membrane of the cells is composed of a hydrophobic lipid bilayer which is poorly permeable to hydrophilic or charged molecules. Indeed, most peptides and proteins are hydrophilic macromolecules, and therefore their diffusion across a tightly sealed hydrophobic cell monolayer is almost negligible. Indeed, epithelial and endothelial cells within mammalian tissues are generally regarded as protective barriers of the body against potentially harmful environmental conditions, and the formation of junctional complexes, especially a so-called tight junction, between epithelial or endothelial cells represents a major mechanism for the construction of these cellular barriers. Unfortunately, these cellular barriers also represent a formidable obstacle for the delivery of drugs to target tissues, especially drugs having large molecular weights such as peptides and proteins.

When drug molecules gain access to the apical membrane of epithelial and endothelial cells, they may pass through the layer of cells by four possible mechanisms (FIG. 2); (a) partitioning into the lipid membrane and diffusing across the cell, a process driven by a chemical potential difference of the compound between two sides of the membrane; (b) passing through water-filled channels, most likely the paracellular junctions between adjacent cells; (c) combining with specific membrane-bound carriers, either energy-independent facilitated diffusion or energy-dependent carrier-mediated transport; and (d) specific or non-specific endocytotic and trascytotic membrane vesicles. Whereas compounds with a molecular weight of less than 1000 can in many instances be transported adequately by any of the above mechanisms, macromolecular drugs (e.g., peptides and proteins), due to their hydrophilic nature, can be transported only by paracellular or by endocytotic and transcytotic mechanisms.

Under physiological conditions, peptides and proteins are normally digested or degraded into small fragments before they are absorbed. Certain macromolecules are known to cross epithelial or endothelial cell walls and gain access to the systemic circulation, albeit generally in very small amounts. The absorption of these molecules is usually either via the paracellular or transcellular pathway. In the paracellular pathway, which occurs only in leaky epithelial cells (e.g., the cells in infant GI-tract, cells in diseased states, or certain cells treated with penetration enhancers), macromolecules are able to pass through the leaky junctions between the cells. The practical use of this route is limited because it does not occur in normal adult tissues. In the transcellular pathway, macromolecules are internalized by cells via membrane-derived vesicles and subsequently transported to the other side of the cells. For purposes of providing a transport method of general applicability, attention has accordingly been focused on the enhancement of macromolecule transepithelial transport via these endocytotic and transcytotic mechanisms.

Endocytosis is the most important process for the cellular uptake and transport of macromolecules in mammalian cells. For example, the transport of nutrients, the regulation of hormone actions, the control of metabolic reactions and processing of antigens all involve endocytosis. In addition, endocytosis is also involved in the transmembrane transport of many toxins and viruses. In endocytosis, exogenous macromolecules, either presented in the surrounding fluid phase or bound to the cell surface, are internalized by the cell via the formation of plasma membrane-derived vesicles. These vesicles with enclosed molecules can be processed through various intracellular organelles and then targeted to their final destinations.

Less than 10% of total cell membrane proteins show specific affinities for certain molecules. These special membrane proteins are usually defined as receptors and molecules which bind specifically to the receptor are defined as ligands. Upon binding, most of these receptor-ligand complexes will be internalized along with the cell membrane through either a clathrin-dependent or a clathrin-independent pathway. In the clathrin-dependent pathway, receptor-ligand complexes are concentrated in clathrin-coated pit regions of the plasma membrane which contribute to about 2% of cell surface area of fibroblasts. The coated pits then invaginate and turn into coated vesicles by pinching off from the cell membrane. After their formation, the coated vesicles lose their coats rapidly, and as a result, smooth membrane vesicles and tubules (endosome) are formed. These endosome-entrapped receptor-ligand complexes are then subjected to a sequence of intracellular processing and sorting events. Most ligands, especially those with important physiological functions such as LDL, Tf, insulin, polymeric IgA, and EGF, enter cells through this pathway. Opportunistic ligands, such as influenza virus and diphtheria toxin, may also exploit this mechanism to enter cells.

The formation of coated pits during receptor-mediated endocytosis has been proposed to occur by two different models. In the first model, it is assumed that coated pits are preformed by assembly of clathrin in the plasma membrane, and in this model, receptors or receptor-ligand complexes are randomly distributed to the pre-existing pits, sequestered within the pits, and endocytosed. In the second model, it is proposed that receptors or receptor-ligand complexes aggregate to form microdomains (or patches) in the plasma membrane, which then trigger the attachment of clathrin to the cytoplasmic tails of receptors. To date, there is insufficient data to determine whether either of these models, or some entirely different mechanism, is in fact operable under normal physiological conditions.

In the clathrin-independent pathway, the invagination of non-coated plasma membrane-derived vesicles is responsible for the endocytosis of receptor-ligand complexes. In general, this type of endocytosis occurs to a much lesser extent of the receptor population and in a less efficient manner as compared to that of clathrin-dependent endocytosis. The exact internalization mechanism of this pathway is still largely unknown. A limited number of ligands, including IgG-ferritin, cholera toxins, ricin, and class I histocompatibility molecules, have been shown to enter cells by this pathway.

Internalization of the membrane receptor can occur with or without the binding of ligands. For example, LDL and transferrin receptors can be concentrated in coated pits and be endocytosed in the absence of bound ligands. On the other hand, insulin receptors will concentrate in coated-pits and be endocytosed only upon binding of an insulin ligand. Different types of ligands can be entrapped in the same coated pits and be internalized in the same vesicle; the divergence of different receptor-ligand complexes occurs at the late stage of the endosome. For example, Tf and EGF have been shown to be taken up in the same vesicles by human epithelial cells and then diverge; EGF goes to the lysosome and Tf is recycled.

In some instances, endocytosis of receptor-ligand complexes is not necessarily required for certain ligands to exert their physiological functions. For example, the binding of EGF and insulin to their receptors alone is sufficient to initiate a physiological response. The endocytosis of receptor-ligand complexes in this case is only responsible for the control of receptor number and the removal of receptor-bound ligands. On the other hand, endocytosis of other complexes, such as the Tf-TfR complex, is required for the physiological function of transferrin (i.e., delivery of ferric ions to the cytosol).

Under physiological conditions, as the cell membrane undergoes constant invagination and turnover, a limited degree of non-receptor mediated endocytosis also occurs. The mechanisms involved in this constant internalization of plasma membranes are still not clear. Solutes in the extracellular fluid or macromolecules non-specifically bound to the cell membrane may be introduced into the cells by this type of endocytosis without the involvement of specific membrane receptors. This type of endocytosis is usually unsaturable and occurs along both clathrin-dependent and clathrin-independent pathways. The internalization of solutes containing fluid is defined as fluid phase endocytosis, and that of the membrane-bound molecules as non-specific adsorptive endocytosis. In fluid-phase endocytosis, a minute droplet of liquid can be randomly enclosed by an invaginated membrane vesicle and then internalized, carrying in whatever solutes happen to be in the droplet. This is an important route for the cell to nonspecifically import extracellular fluids in which nutrients and other important molecules are contained. As fluid-phase endocytosis does not require a membrane receptor, the uptake is dependent only on the concentration of the macromolecules in the extracellular fluid and the rate of membrane internalization. Because most of the endocytosed contents are usually targeted to and degraded in lysosomes, this route may not be useful for drug transport across the cells. In adsorptive endocytosis, non-specific cell membrane-bound molecules will be internalized via membrane invagination, the majority of which will eventually also be targeted to and degraded in lysosomes. This pathway is non-saturable at low concentrations, but it may be saturable at high concentrations due to limits on membrane-binding sites and on the rate of membrane internalization. As a consequence, endocytosis does not appear to provide a viable mechanism for generalized transport of active agents across the walls of endothelial or epithelial cells.

Transcytosis is the transcellular transport of internalized vesicles from their sites of entry to the opposite surface of the cell. The contents enclosed in the vesicles, (i.e., solutes in the fluid phase or specifically or non-specifically membrane-bound molecules) are then released undegraded into the extracellular fluid. The initial cell membrane internalization processes of transcytotic vesicles usually share identical mechanisms with that of endocytotic vesicles; however, the intracellular sorting events differentiate the ultimate destination of transcytotic and endocytotic vesicles.

Transcytosis occurs in many type of cells, such as placental syncytiotrophoblasts, enterocytes of the small intestine, colostrum cells, liver epithelial cells and endothelial cells. The main functions of transcytosis are believed to be the distribution of membrane-impermeable molecules (especially of macromolecules between separated biological compartments) and maintenance of a distinct cell membrane polarity. Transcytosis can be receptor-mediated or non-receptor mediated; for example, the transcytosis of albumin, cationized albumin, transferrin, IgG, thyroglobulin, nerve growth factor, EGF, ricin, and insulin have been shown to be mediated by receptors, whereas the transcytosis of HRP, Ferritin, dextran and lectin wheat germ agglutinin proceed via a non-specific mechanism. Transcytosis in polarized epithelial cells occurs in a vectorial fashion. For example, transcytosis of IgG, thyroglobulin, nerve growth factor, EGP and ricin occur in the apical-to-basal direction; the transcytosis of IgA and Tf usually occur in the basal-to-apical direction. Transcytosis via a non-specific mechanism usually occurs at a very low rate.

A sequence of intracellular sorting and processing events determines the ultimate fate of plasma membrane-derived vesicles. Different cells may process membrane vesicles containing the same receptors in a different manner, and even a single cell may process the same vesicles in different ways at different times. The underlying mechanisms of sorting and processing of these internalized membrane vesicles as well as the intracellular and extracellular conditions which can affect the sorting events are still largely unknown.

Endosomes, the Golgi apparatus, and possibly the ER have been considered the sorting compartments for internalized vesicles. Lysosomes, on the other hand, have been considered the end-points where the vesicles (as well as their contents) are degraded. Although the detailed sorting events and the associated mechanisms that determine the intracellular routing of the internalized vesicles is not yet known, available data indicate that the signals in the cytoplasmic tail of membrane receptors and the extracellular environments may play a role.

Although the exact intracellular sorting and processing mechanisms remain to be elucidated, the apparent routing of the vesicles can be characterized in several ways. One involves receptor recycling and ligand degradation; in this route, dissociation of ligands from their receptors occurs within acidic endosomes. The released ligands are then delivered to a lysosomal compartment, where they are degraded; the membrane-bound receptors leave the endosome by budding off as a membrane vesicle and recycling back to the cell surface to bind new ligands from the extracellular fluid. Many ligand-receptor complexes, such as LDL, asialoglycoproteins, and transcobalamine II undergo this intracellular routing.

In accordance with another mechanism, both receptor and ligand are degraded. The EGF receptor is an example for this route. Although EGF dissociates from its receptor in the endosome due to the acidic pH, the receptor does not segregate into a separate vesicle for recycling back to the cell surface. Instead, both EGF and its receptor eventually reach a lysosome where both are degraded. Other ligands such as multivalent IgG, interferons and their receptors also follow this pathway.

Pursuant to yet another mechanism, both receptor and ligand are transported. This route is usually utilized in the transcellular transport of macromolecules across endothelial and epithelial cells. A typical example of this route is the transcellular transport of maternal IgG across the intestinal lining of epithelial monolayer in neonates. Once the IgG binds to its receptor on the cell, the complex is internalized; instead of reaching lysosomes or recycling back to the cell surface, the complex is transported to the other side of the cell where the IgG is released. Secretory IgA (sIgA) and its receptor also follow this route, but in an opposite direction; the receptor is partially degraded during the transcellular process and released together with IgA as a secretory component.

In a final type of routing mechanism, both receptor and ligand recycle to the cell surface. Transferrin, a major serum glycoprotein which transports iron into cells, is a typical example for this route. After entry into an endosome, TfR-bound diferric Tf releases iron due to the low-pH environment of the endosomes. The resultant apotransferrin remains bound to its receptor, due to its high affinity for the receptor under acidic pH. Thereafter, apo-Tf-receptor complexes are segregated into a vesicle and recycled back to the cell surface. Other ligands, such as intrinsic factor and class I and II MHC molecules, may also follow this pathway.

Three main factors limiting the penetration of active agents, and in particular peptide and protein drugs, across cells: the physicochemical properties of the drugs; the environment in the vicinity of the cells; and the membrane structure and the biological function of the cells. Many approaches have been designed and developed to minimize the above factors and therefore to increase drug penetration across the cells. Incompatibility with the lipid molecules in the cell membrane (hydrophilicity and hydrogen-bonding capacity), large molecular size and lability to proteolytic and hydrolytic degradation are unique properties associated with peptide- and protein-based drugs. Chemical modifications (prodrug approaches) and chemical systheses of analogues (analogue approaches) have been explored; to date, both types of approach have been of only limited applicability.

Another category of approach involves altering the environment in the vicinity of the epithelial or endothelial cells. There are two major routes for large macromolecules (e.g., peptide and protein drugs) to pass through an epithelial or endothelial cell monolayer: the paracellular pathway, which is normally sealed by the tight junctions that exist between adjacent cells; and the transcellular pathway, which is normally obscured by the hydrophobic lipid bilayer of the cell membrane.

Various types of enhancers, which act either by relaxing the tight junction or by increasing the fluidity (and hence, the permeability) of the membrane, have been developed to increase drug transport across the cells. Although some degree of success has been achieved, these approaches suffer from non-specificity and toxicity. When the tight junction is opened up by selected enhancers, substances other than the intended agents may also pass through the open gap between the cells, causing undesirable effects. Moreover, the perturbation of the cell membrane by enhancers can be harmful and toxic to the cells; irritation and inflammation of local tissues after the use of enhancers has been reported.

In eukaryotic cells, there is an interconnected membrane traffic network responsible for a constant cellular membrane internalization. The half-life of membrane turnover in fibroblasts has been shown to be 2 hours and in macrophages, 0.5 hour. In epithelial cells, constant renewal of the brush-border membrane and membrane-associated proteins/glycoproteins has also been reported. The formation of membrane vesicles was shown to occur at a rate of 3000 vesicles/cell/min, or 5-50 times the cell-surface area per hour in liver epithelial cells. These membrane vesicles are naturally used to ingest macromolecules by endocytosis, to discharge their secretory products by exocytosis, or to transport macromolecules from one side of cell to the other by transcytosis.

One of the most notable cellular barriers which drug delivery formulations attempt to circumvent is the blood-brain barrier (BBB), which is composed of 95% brain capillary endothelium. Clinical observations indicate that drug delivery across the BBB is a major factor in the management of the many central nervous system (CNS) diseases, such as primary or metastatic tumors in the brain, primary or secondary CNS infection in AIDS, neurological degenerations in Parkinson's disease, multiple sclerosis, and genetic enzyme deficiencies.

Several approaches have been considered in an attempt to increase the transport of impermeable drugs across the BBB. For an approach to be clinically applicable, such a method must fulfill at least the following three criteria: (1) reversibility—the increase in permeability of the BBB must be transient and controllable, and should not cause permanent changes in transendothelial resistance; (2) nontoxicity—the increase in permeability of the BBB should not damage the endothelial cells, and more importantly should not cause any neurotoxicity; and (3) selectivity—the increase in permeability should be effective only for the transport of the therapeutic drug to the target tissue, but not induce transport of other potentially-harmful molecules or cause deposition into non-targeted tissues.

Unfortunately, among the currently available penetration enhancers for epithelial and endothelial drug absorption, none can adequately fulfill these criteria. Their use in therapeutics is generally unreliable and sometimes quite dangerous; hence, the use of these techniques should be considered with extensive caution. In fact, to date the only clinically-acceptable method for increasing the BBB permeability is the osmotic disruption of endothelial junctions by hypertonic treatment. Although this method is indeed reversible, it can cause severe neurotoxicity due to its lack of selectivity. Hypertonic treatment extensively loosens BBB tight junctions and indiscriminately increases the paracellular transport of many impermeable molecules from the blood, which may include many pathogens and toxins. As reported in a clinical study, 5% of the patients who received a single osmotic disruption treatment developed a stroke, and 14% experienced various other types of seizures [Neuwelt, E. A. and Dahlborg, S. A. (1989) in *Implications of the Blood-Brain Barrier and Its Manipulation*, Plenum Publishing Co., New York, Vol. 2, pp. 195-261]. Other complications associated with this treatment include brain edema and ocular toxicity. Despite their inherent risk of side effects, osmotic disruption procedures, such as arterial infusion of hypertonic mannitol solution [Neuwelt, E. A., Barnett, P. A., Hellstrom, I., Hellstrom, K. E., Beaumier, P., McCormick, C. I. and Weigel, R. A. (1988) *Cancer Res.* 48, 4725-4729; Neuwelt, E. A., Frenkel, E., Gumerlock, M. K., Braziel, R., Dana, B. and Hill, S. A. (1986) *Cancer* 58, 1609-1620], are still being used to increase the transport of antibodies and drugs to the brain of the patient for the diagnosis or therapeutic treatment of brain tumors. Therefore, it can be anticipated that if a safe procedure could be achieved for the selective increase of specific drugs or proteins transport across the BBB, the treatment of many CNS-associated diseases would be markedly improved.

One potentially promising route to achieve selective delivery of a drug or protein across epithelial or endothelial cells is to use receptors as markers and receptor-building ligands as vehicles for their transcellular transport [Rodman, J. S., Mercer, R. W. and Stahl, P. D. (1989) *Current Opinion in Cell Biology* 2, 664-672]. This type of carrier-mediated transport is known as receptor-mediated transcytosis, which has been demonstrated in epithelial and endothelial cells for the transport of hormones [King, G. L. and Johnson, S. M. (1985) *Science* 227, 1583-1586], albumin [Ghitescu, L., Fixman, A., Simionescu, M. and Simionescu, N. (1986) *J. Cell Biol.* 102, 1304-1311], and immunoglobulins [Rodewald, R. (1980) *J. Cell Biol.* 85, 18-32; Underdown, B. J. (1989) *Immunol. Invest.* 18, 287-297]. Drug delivery via receptor-mediated transcytosis is highly specific because it enhances only the transport of molecules that are conjugated to receptor-binding ligands. In addition, drug delivery via transcytosis is also specific for receptor-bearing cells, and therefore, a targeted delivery system can be developed [Gregoriadis, G., Poste, G., Senior, J. and Trouet, A. (eds.), *Receptor-Mediated Targeting of Drugs*, Plenum Press, New York (1984)].

One type of receptor which has been suggested to be a potential vehicle for transcytotic transport across the BBB is the transferrin (Tf) receptor (TfR). Tf is a natural transport protein for iron [Aisen, P. and Listowsky, I. (1980) *Ann. Rev. Biochem.* 49, 357-393], and TfR's are expressed abundantly on the luminal surface of the brain capillary endothelium [Jefferies, A. E., Brandon, M. R., Hunt, S. V., Williams, A. F., Gatter, K. C. and Mason, D. Y. (1984) *Nature* 312, 162-163]. Unlike the binding of hormones or growth factors to their receptors, the binding of Tf to its receptor will not alter any metabolic or physiologic pathway in the endothelial wall. In addition, the intracellular accumulation of internalized Tf or TfR is negligible due to the efficient recycling of the TfR to the cell surface [Fuller, S. D. and Simons, K. (1986) *J. Cell. Biol.* 103, 1767-1779]; therefore, less drug toxicity would result for the epithelial or endothelial cells.

Despite these promising characteristics of receptor-ligand interaction, receptor-mediated transcytosis has so far failed to demonstrate to be an effective means for increasing transepithelial or trasendothelial drug transport. One of the major drawbacks of drug delivery via transcytosis is that the rate of transport by this mechanism is usually very low due to the polarized distribution of receptors on the apical and basal plasma membranes. This membrane polarity renders surface receptors or markers difficult to traverse across epithelial or endothelial cells.

For example, TfR's have been found to reside predominantly on the basal membrane of MDCK epithelial cells. Because of this polarized distribution, basal membrane-associated TfR's recycle efficiently to their original membrane domain. Consequently, less than 0.16% of basal membrane-bound Tf can be transcytosed to the apical surface [Fuller et al., supra]. When an anti-TfR antibody was used as a transport carrier for methotrexate, it was found that only 0.27% of the injected dose of the drug reached the brain parenchyma in 24 hr following i.v. injection [Friden, P. M., Walus, L. R., Musso, G. F., Taylor, M. A., Malfroy, B. and Starzyk, R. M. (1991) Proc.Natl.Acad.Sci. USA 88, 4771-4775]. Similar results have also been reported in the case of acetylated low-density lipoprotein, where a high affinity of this protein to the luminal surface receptor of the brain capillary endothelium resulted in only a negligible absorption by the brain parenchyma [Triguero, D., Buciak, J. and Pardridge, W. (1990) J. Neurochem. 54, 1882-1888 (1990)]. This discrepancy between the high receptor density on the capillary surface and the low ligand transport to the brain parenchyma indicates that the translocation of ligand-receptor complexes across endothelial cells may be the rate limiting step in the receptor mediated trans-BBB drug delivery by macromolecular carriers. Nonetheless, present knowledge regarding the control and regulation of transcytosis in polarized cells especially in brain capillary endothelium, is still very limited.

Receptor-mediated transcytosis in epithelial and endothelial cells is one of the major pathways by which many hormones, growth factors, and other proteins are distributed within mammalian tissues and is a highly regulated process in membrane-polarized cells [Mostov, K. E., and Simister, N. E. (1985) Cell 43, 389-390; Simionescu, M. (1989) in Endothelial Cell Biology in Health and Diseases, (Simionescu, N., and Simionescu, M., eds.) pp. 69-104, Plenum Press, New York]. It has been shown that although both receptors of epidermal growth factor (EGF) and transferrin (Tf) are localized on the basolateral membrane of filter-grown Madin-Darby canine kidney (MDCK) epithelial cells [Maratos-Flier, E., Yang Kao, C.-Y., Verdin, E. M., and King, G. L. (1987) J. Cell Biol. 105, 1595-1601; Fuller, S. D., and Simons, K. (1986) J. Cell Biol. 103, 1767-1779], only EGF can be transcytosed across the cell monolayers [Maratos-Flier et al., supra] while Tf remains exclusively in the recycling pathway of the basolateral membrane [Fuller et al., supra]. Factors that accurately control vectorial transcytosis of membrane-associated receptors and their bound ligands in polarized cells have been a subject of active investigation in recent years [Rodriguez-Boulan, E., and Salas, P. J. I. (1989) Annu. Rev. Physiol. 51, 741-754.; Breitfeld, P. P., Casanova, J. E., Simister, N. E., Ross, S. A., Mckinno, W. C. and Mostov, K. E. (1989) Current Opinion in Cell Biol. 1, 617-623; Rodman, J. S. , Mercer, R. W. and Stahl, P. D. (1990) Current Opinion in Cell Biol. 2, 664-672 [. It has been shown that amino acid sequence, phosphorylation of the cytoplasmic tail [Davis, C. G., van Driel, I. R., Russell, D. W., Brown, M. S., and Goldstein, J. L.(1987) J. Biol. Chem. 263, 4075-5082 ; Glenney, J. R. (1988) Cell 52, 675] of receptors, and cytosolic factors [Balch, W. E. (1989) J. Biol. Chem. 264, 16956-16968] can affect the internationization and intracellular trafficking of membrane receptors.

It is an object of the present invention to enhance the carrier-mediated transcytosis of active agents, such as monomeric organic molecules and proteins, in endothelial and epithelial cells.

SUMMARY OF THE INVENTION

In accordance with the present invention, transepithelial and transendothelial delivery of active agents, in particular peptides and proteins, is substantially enhanced through the use of the following combinations: (1) a conjugate carrier for the active agent comprising a ligand for a particular cell-surface receptor which undergoes endocytosis and/or transcytosis; and (2) and accelerator for the transcytosis of the particular cell-surface receptor. For example, certain agents (such as monensin and brefeldin A) can reversibly disrupt the polarized distribution of TfR's and markedly increase the rate of receptor-mediated transcytosis of Tf. Because this increase in transcytosis is specific to the cell-surface receptors (e.g., TfR), no other molecules will be co-transported with the receptor/ligned combination unless they have been conjugated to the ligand.

Pursuant to a preferred embodiment of the present invention, there is provided a drug-delivery system comprising: (1) a carrier molecule selected from the group consisting of transferrin receptor ligands to which an active agent of interest may be conjugated; and (2) a transport enhancing agent (e.g., monensin or BFA) which enhances transendothelial or transepithelial transport of the transferrin receptor ligand/active agent conjugate via the TfR's.

BRIEF DESCRIPTION OF THE DRAWINGS

The invention may be better understood with reference to the accompanying drawings, in which.

DETAILED DESCRIPTION OF THE INVENTION

Figure 1A:
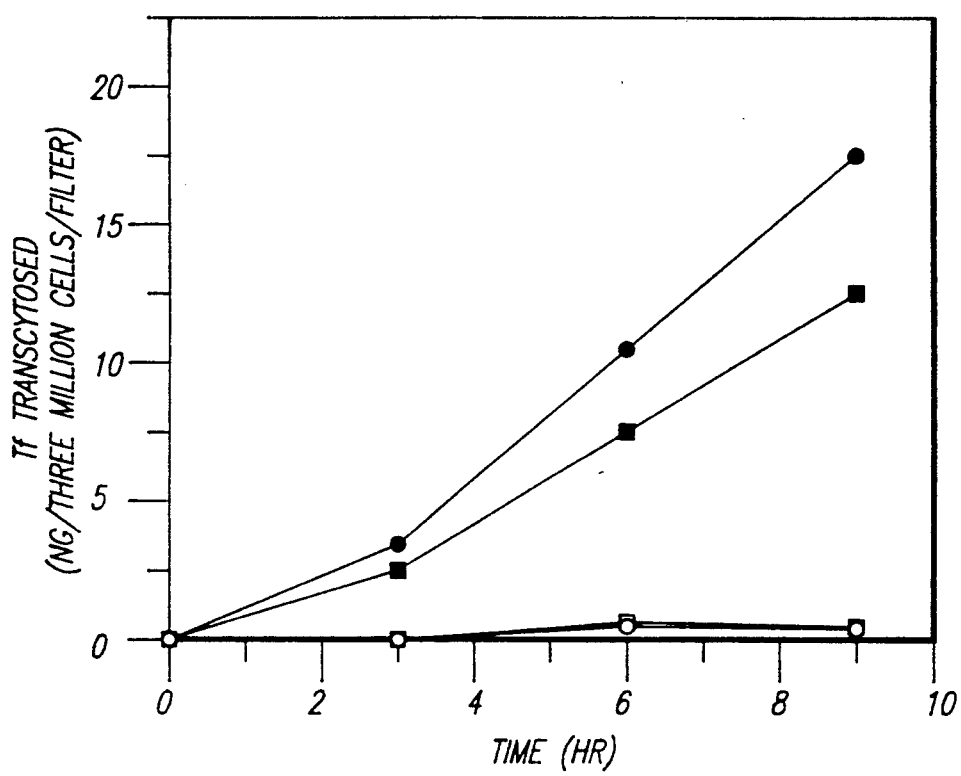
FIGS. 1A and 1B illustrate the levels of transcytosis of $^{125}$I-Tf and HRP achieved in filter-grown MDCK cells, respectively.

The present invention involves the use of non-specific and specific-membrane binding ligands as well as the use of agents which can perturb intracellular protein sorting processes to significantly increase the transport of a macromolecular protein across the cells via endocytotic and transcytotic mechanisms.

During the last decade, most of the studies on drug transepithelial transport have been carried out at tissue and organ levels. For example, various types of intestinal samples, such as everted intestine preparations, intestinal ring slices and mucosal sheets have been used. Because of such factors as cellular heterogeneity, complexity in geometric structure, inaccessibility of the serosal side of the epithelium, and limited viability of epithelial cells in the isolated tissues, it is very difficult to use these methods for specific mechanistic studies on transepithelial transport of the drugs.

Purified brush border membrane vesicles, basolateral membrane vesicles and isolated intestinal epithelial cells have also been used to study drug transport. Although membrane vesicles offer an excellent model to study transport properties of solutes without the interference of cellular metabolism, they may not be suitable for studies on the endocytosis and transcytosis of macromolecules because of lack of membrane internalization. In addition, results from these membrane vesicles may not correlate well with those from viable cells. Isolated intestinal epithelial cell is a very good model to study the cellular binding, uptake and transport of drugs, but it suffers from short viability; therefore, the practical use of this type of cell is limited.

Cultured filter-grown epithelial cells, on the other hand, show many advantages as a model system. For example, the viability of the cell can be maintained for almost as long as it is needed, and studies on the interaction between peptides/proteins and cells can be carried out readily without the potential interference from other mucosal structures which are normally found in tissue samples. In addition, filter-grown epithelial cells allow easy access to both apical and basal side of the cell. The experimental data obtained is generally more reliable and easy to interpret, because of the relative homogeneity of the cell population. Other desirable properties, such as high sensitivity, reproducibility, and small sample requirements, are also intrinsic to cultured epithelial cell models.

Several epithelial cell lines, such as dog kidney epithelial cells and human colon epithelial cells, have been developed in culture [see, e.g., Chantret, I., Barbat, A., Dussaulx, E., Bratain, M. G., and Zweibaum, A., (1988) *Cancer Research* 48, 1936–1942; Rodriguez-Boulan, E. and Nelson, W. J. (1989) *Science* 245, 718–725]. For model purposes, the MDCK and Caco-2 cell lines have been recognized as particularly useful.

The MDCK cell line displays many features of in vivo epithelial cells when grown under cultured conditions. In addition, its morphogenesis and polarity have been extensively characterized in the literature [see, e.g., Gonzalez-Mariscal, L. (1985) *J. Membr. Biol.* 86, 113–125; Rodriguez-Boulan, supra]. This cell line was originally derived from dog kidney epithelial cells, and has been recently characterized as a model system for transepithelial drug transport studies [Cho, M. J., Thompson, D. P., Cramer, C. T. (1989) *Pharm. research.* 6, No. 1]. The MDCK cell line shows brushborder, lateral spaces, polarity of the cellular plasma membranes, and appropriate enzyme makers [Rodriquez-Boulan, supra]. This cell line also displays a good apical cell to cell tight junctions as indicated by very high transepithelial electrical resistance (TEER, about 3000 ohms cm$^2$) [Gonzalez-Mariscal, supra].

The Caco-2 cell line is the only one among twenty human colon carcinoma epithelial cell lines tested that shows spontaneous enterocytic differentiation, as characterized by a polarization of the cell layer with the formation of domes and the presence of an apical brush border [Chantret, supra]. It has been shown that when grown-in filter membranes, Caco-2 cells also exhibit many intestinal epithelial characteristics, i.e., brush-border microvilli, brush border enzymes, and tight junctions [Pinto, M., Robine-Leon, S., Appay, M. D. et al. (1983) *Biology of the Cell* 47, 323–330; Grasset, E., Pinto, M., Dussaulx, E., Zweibaum, A. and Desjeux, J. F. (1984) *Am. J. Physiol.* 247 (*Cell Physiol.* 16), C260–C267; Hidalgo, I. J., Raub, T. J., and Borchardt R. T. (1989) *Gastroenterology* 96, 736–749]. The brush border of these cells has been shown to contain many hydrolases such as sucrase-isomaltase, lactase, alkaline phosphatase, aminopeptidase N, and dipeptidylpeptidase IV [Chantret, supra]. Brushborder enzymes indigenous to the adult human small intestine are increasingly produced during growth [Hidalgo, supra]. So far, this cell line has been used as a model for many studies relating to gastrointestinal drug absorptions [Hidalgo, supra; Artursson, P. (1990) *J. Pharm. Sci.* 79, 476–482; Heyman, M., Crain-Denoyelle, A. M., Nath, S. K., and Desjeux, J. F. (1990) *J. Cell Physiol.* 143, 391–395; Wilson, G., Hassan, I. F., Dix, C. J., Williamson, Shah, R., Mackay, M. (1990) *J. Controlled Release* 11, 25–40]. One drawback of this cell line is that it does not offer as high a TEER as the MDCK cell line does (its TEER is only about 500 ohms cm$^2$); nonetheless, it is a better physiological model for human intestinal epithelial cells.

Among several candidates, transferrin was selected as a model ligand for use in conjugation of active agents to be transported. Tf receptors exist in high amounts and in a highly polarized manner in epithelial cell models. Moreover, the recycling accuracy of Tf in MDCK cells is about 99% [Fuller, S. D. and Simmons, K. (1986) *J. Cell Biol.* 103, 1767–1779]; therefore, the chemical-induced Tf transcytosis as well as changes in receptor recycling and distribution can be easily and accurately detected. Furthermore, because Tf undergoes a rapid recycling with a half life of 3–15 min after internalization and its intracellular routing excludes a lysosomal compartment [Dautry-varsat, A., Ciechanover, A. and Lodish, H. F. (1983) *Proc. Natl. Acad. Sci.* USA 80, 2258–2262; Klausner, R. D., Ashwell, G., Van Renswoude, J., Harford, J. B. and Bridges, K. R. (1983) *Proc. Natl. Acad. Sci.* USA 80: 2263–2266], high efficiency of transport and limited intracellular degradation can be expected if its transcytosis is induced. In addition, monoclonal antibodies specific to the TfR are known and commercially available (for example, from Dako Corporation, Santa Barbara, Calif. and Boehringer Mannhein Biochemicals, Indianapolis, Ind.). Of course, it is equally possible to use conventional methods to generate polyclonal or monoclonal antibodies to the TfR or other receptors directly for use in formation of suitable conjugates.

For the purpose of studying macromolecular transport across epithelial cells, horseradish peroxidase (HRP) was selected as a probe protein. This protein does not naturally occur in mammalian cells, it has a fairly large molecular weight (MW=40,000) which is a good representative of potential protein drugs, and it is an enzyme whose enzymatic activity can be easily detected at a low concentrations ($10^{-9}$ g/ml) [Worthington Manual (1988) pp. 254-260, Worthington Biochemical Corporation, Freehold, N. J.]. HRP is thus a very useful marker for determining if the protein transported via the endocytotic and transcytotic pathway still maintains its biological activity.

Figure 5A:
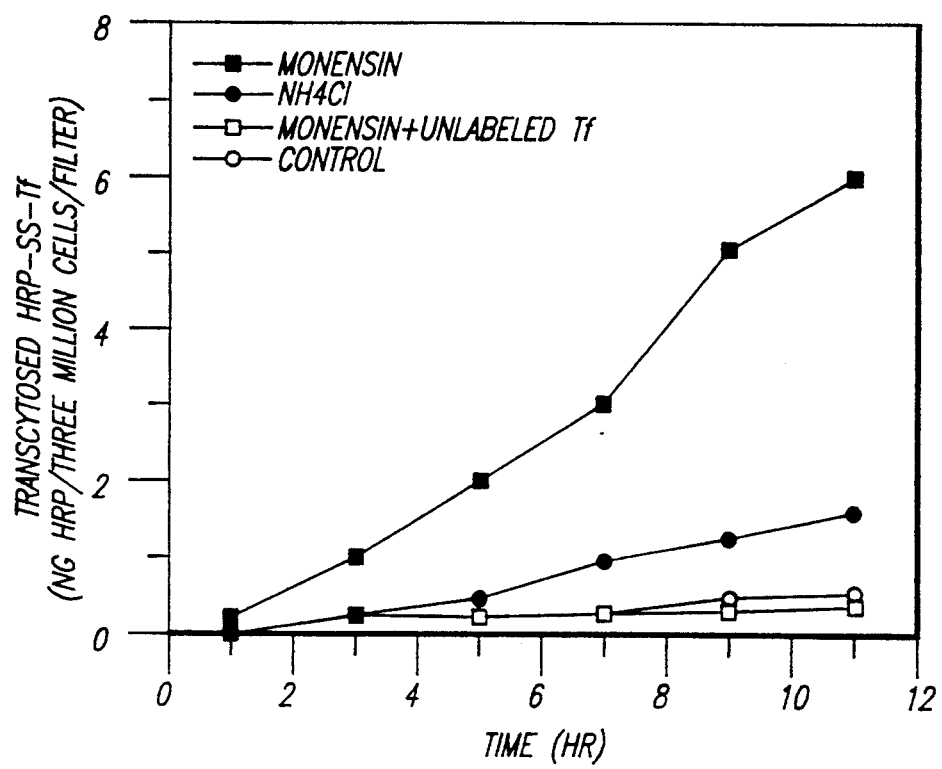
FIGS. 5A and 5B illustrate the results of experiments to determine the effects of monensin and NH$_4$Cl on the transcytosis of HRP-SS-Tf (FIG. 5A) and HRP (FIG. 5B)
Figure 5B:
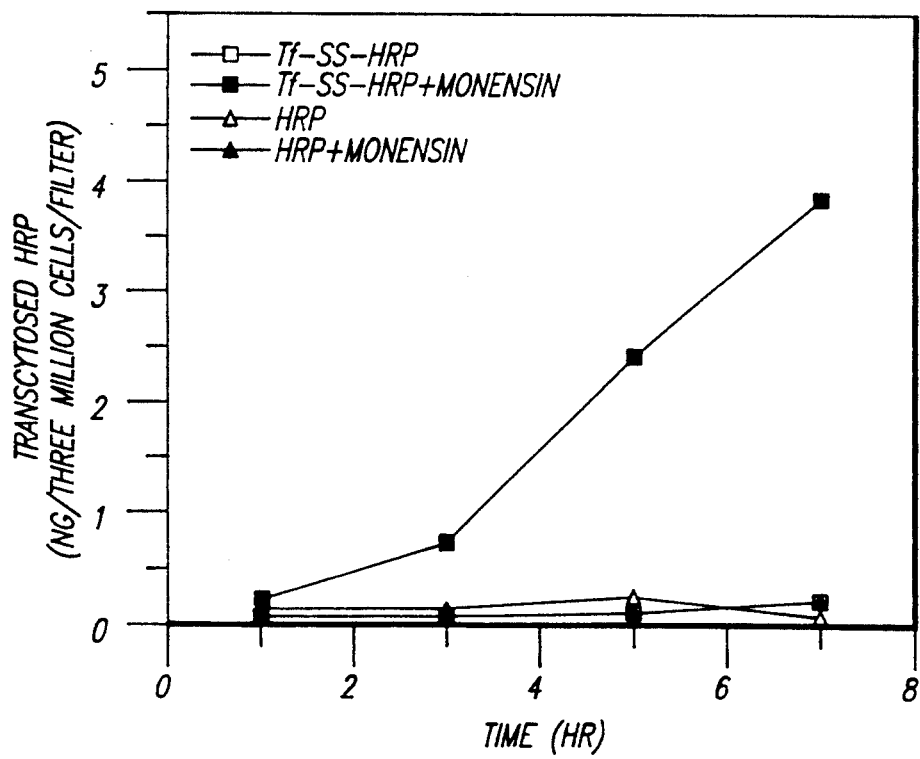
Figure 6A:
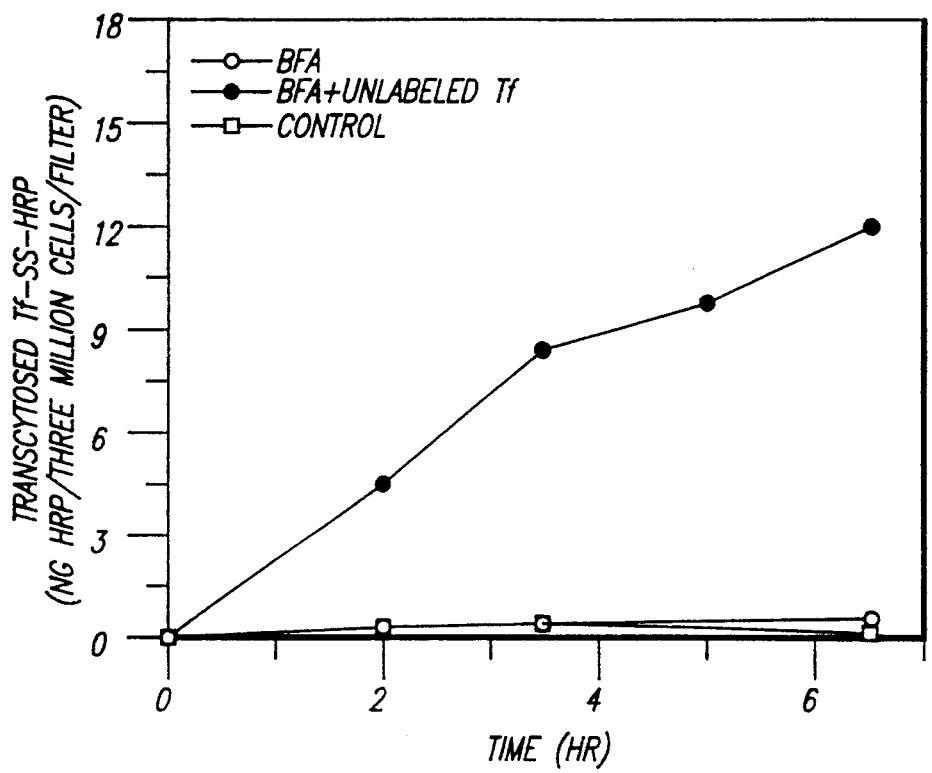
FIGS. 6A and 6B illustrate the results of experiments to determine the effects of BFA on the transcytosis of HRP-SS-Tf and HRP, respectively.
Figure 6B:
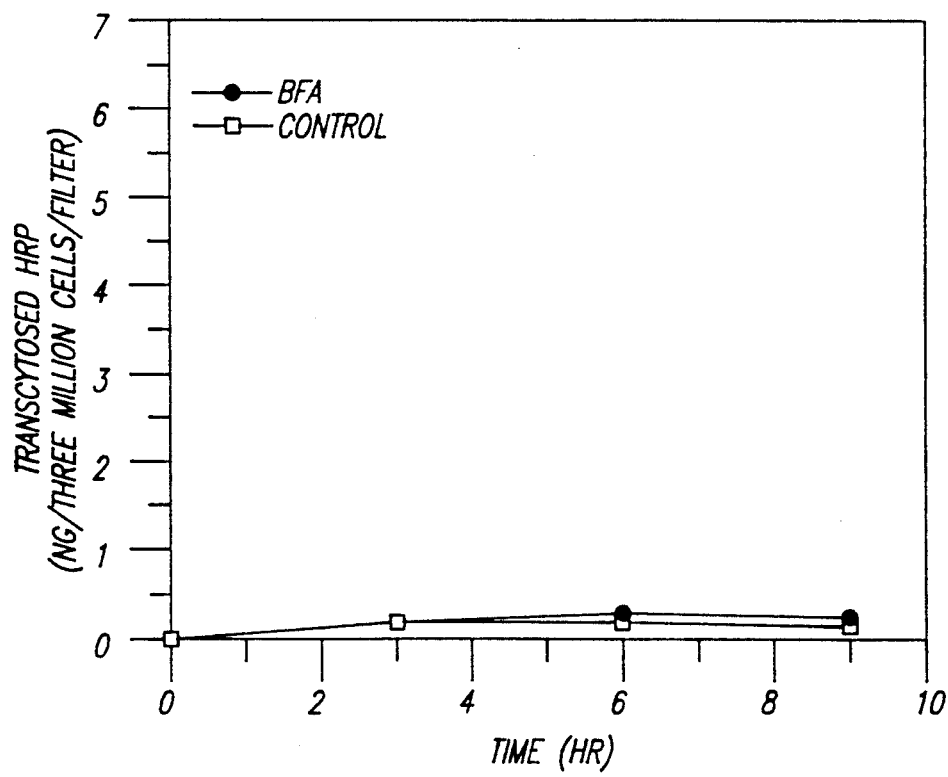

The Tf transported via the enhanced transcytotic pathway showed a specific binding affinity for TfR on K562 cells, indicating that its biological activity was retained. This enhanced Tf transcytosis was not due to drug-induced leakage of or damage to the cell monolayers, because the same drug-treatment did not increase the transport of the fluid phase marker HRP (FIGS. 5B and 6B). The addition of unlabeled Tf and incubation at 25° C. strongly reduced the enhanced transcytosis, indicating that the transcytosis is a receptor-mediated active process.

The present invention demonstrates for the first time that the receptor-mediated Tf transcytosis can be enhanced to a high extent in epithelial cells. Furthermore, Tf was also shown to carry covalently-linked HRP across the cells via an enhanced transcytotic pathway and the increase of HRP transcytosis was about 10 to 25 fold, respectively (FIGS. 5A and 6A). These data demonstrate the feasibility of using this enhanced transcytotic pathway to deliver other macromolecules across epithelial cells. A salient feature of the present invention is the use of transport accelerators, such as monensin and BFA, to achieve acceptable levels of conjugate transport.

Monensin and NH$_4$Cl are known for their effects on dissipating the pH gradients across acidic organelle membranes and alkalizing the intracellular acidic compartments, including endosomes, lysosomes, and the Golgi apparatus [Maxfield, F. R. (1982) *J. Cell Biol.* 95, 676-681; Mollenhauer, H. H., Morre, D. J. and Rowe, L. D. (1990) *Biochimica et Biophysica Acta* 1031, 225-246]. However, their mechanisms of action are quite different. Monensin, a hydrophobic ionophore, acts by partitioning into the lipid bilayer and exchanging H+ with cations, especially Na+ [Mollenhauer, supra] between the membranes. NH$_4$Cl, on the other hand, acts by simple diffusion of NH$_3$ across the membrane and accumulation of NH$_4$+ in the acidic lumen [DeDuve, C. (1983) *Eur. J. Biochem.* 137, 391-397]. Since acidification in endosomes plays a crucial role in the dissociation of ferric ions from Tf as well as the sorting of TfR-Tf complexes to the recycling pathway [Dautry-Varsat, supra], both NH$_4$Cl and monensin have been shown to prevent the release of Tf from the cells [Klausner, supra; Stein, B. S., Klaus, G. B., and Sussman, H. H. (1984) *J. Biol. Chem.* 259, 14762-14772]. The increased Tf accumulation in MDCK and Caco-2 cells in presence of NH$_4$Cl and monensin, therefore, can be explained by effects of the drugs on acidic organelles.

NH$_4$Cl (5 mill) has been shown to elevate the intracellular pH in MDCK cells to a the same degree as monensin (6 μM) [Maxfield, supra]. In experiments, NH$_4$Cl at concentrations as high as 10 and 20 mM induced an increase in Tf transcytosis which was less than 1/7 of that by monensin (6 μM). These results suggest that the enhanced Tf transcytosis by monensin is unlikely solely due to elevation of the intracellular pH.

The fact that the same increase of cellular accumulation of Tf by NH$_4$Cl and monensin treatment does not give same increase in the transcytosis of Tf implies that monensin enhanced Tf transcytosis does not occur via passive diffusion. If the transcytosis is governed by a passive diffusion processes, the same amount of Tf accumulated in both monensin- and NH$_4$Cl-treated cells would have resulted in the same extent of diffusion of Tf from an intracellular pool to the culture medium.

On the other hand, the slight increase in Tf transcytosis in NH$_4$Cl-treated cells (Table 4) as compared to control cells may be explained by the elevated intracellular pool of Tf. It is possible that the highly accumulated Tf in NH$_4$Cl treated cells can diffuse more readily across the cells as compared to that in control cells.

It is know that heavy membrane traffic from the cell surface to stacked Golgi cisternae and secretory granules or vacuoles in regulated and non-regulated secretory cells [Herzog, V. and Farquhar, M. G. (1977) *Proc. Natl. Acad. Sci. USA* 745, 5073-5077; Farquhar, M. G. (1978) *J. Cell Biol.* 77, R35-42] can occur. This plasmalemma to Golgi traffic is probably related to the recycling of the membrane which can be used as containers for the packaging of secretory products [Farquhar, M. G. (1981) *Methods Cell Biol.* 23, 399-427; Farquhar, M. G., in Membrane Recycling, Evered, D. and Collins, G. M. eds., Pitman Books Ltd., London 157-174 (1982)]. It has been shown that the recycling plasmalemmal TfR can visit most, if not all Golgi sub-compartments [Woods, J. W., Doriaux, M. and Farquhar, M. G. (1986) *J. Cell Biol.* 103, 277-286], and that Golgi-associated post-translational modification of TfR as well as Tf can occur [Snider, M. D. and Rogers, O. C. (1985) *J. Cell. Biol.* 100, 826-834]. Although the role of the Golgi-associated modification of TfR and Tf has not been elucidated, it is speculated that this modification may determine the subsequent intracellular routing of the TfR-Tf complexes. Such a Golgi-associated modification of proteins has been shown to be responsible for the targeting of lysosomal enzyme proteins to the lysosomal compartments [Pohlmann, R. S., Waheed, A., Hasilik, A. and van Figura, K. (1982) *J. Biol. Chem.* 257, 5323-5325; Goldberg D. E. and Kornfeld, S. (1983) *J. Biol. Chem.* 258, 3159-3165].

In addition to the elevation of pH, monensin has many other effects [see Mollenhauer, supra], and its principal action site has been proven to be within the Golgi complex. It has been shown that monensin can specifically disassembles the trans-Golgi apparatus by its ionophore function [Stein, 1984, supra; Stein, B. S. and Sussman, H. H. (1986) *J. Biol. Chem.* 261, 10319-10331].

Brefeldin A (BFA) is a fungal metabolite known to perturb secretory protein transport from the ER to the cell surface [Harri, E., Loeffler, W., Sing, H. P., Stahelin, H. and Tamm, C. (1963) *Helv. Chim. Acta* 46, 1235-1243; Takatsuki, A., and Tamura, G. (1985) *Agric. Biol. Chem.* 49, 889-902; Misumi, Y., Misumi, Y., Miki, K., Takatsuki, A., Tamura, G., and Ikehara, Y. (1986) *J. Biol. Chem.* 261, 11398-11403; Magner, J. A., and Papagianner, E. (1988) *Endocrinology* 122, 912-920; Fujiwara, T. Oda, K, Yokota, S., Takatsuki, A., and Ikehara, Y. (1988) *J. Biol. Chem.* 263, 18545-18552]. Pursuant to one preferred embodiment of the present invention, BFA is employed to markedly enhance receptor-mediated transcytosis of Tf (and any agent associated therewith) and cause transferrin receptor (TfR) redistribution in MDCK epithelial cells.

On the other hand, monensin has also been shown to radically slow the intracellular transport of newly synthesized secretory proteins and their residing membrane vesicles [Tartakoff, A. M. (1983) Cell 32, 1026-1028]. BFA also has been shown to curtail the vesicular transport of secretory proteins from the ER via cis- and trans-Golgi elements to the cell surface, possibly by its effects on blocking the association of B-COP, a non-clathoursin coating protein, to the Golgi membrane and preventing the formation of non-clathoursin coated vesicles budding from the cis-Golgi apparatus [Orci, L., Tagaya, M., Amherdt, M., Perrelet, A., Donaldson, J. G., Lippincott-Schwartz, J., Klausner, R. D. and Rothman, J. E. (1991) Cell 64, 1183-1195]. Therefore, as an alternative mechanism, the inhibition of outwardly directed vesicle transport by monensin and BFA may indirectly affect the traffic pattern of incoming TfR-Tf containing endocytotic vesicles, presumably by decreasing the interaction between the two types of vesicles.

The underlying mechanism for BFA-induced missorting and transcytosis of the TfR are not fully understood at the present time. BFA has been shown curtail secretory protein transport to the cell surface [Takatsuki et al., supra; Misumi et al., supra; Magner et al., supra; Fujiwara et al., supra], to interfere with protein traffic between the ER and the Golgi complexes [Misumi et al., supra; Oda, K., Hirose, S., Takami, N., Misummi, Y., Takatsuki, A., and Ikehara, Y. (1987) FEBS Lett. 214, 135-138; Perkel, V. S., Liu, A. Y., Miura, Y., and Magner, J. A. (1988) Endocrinology 123, 310-318; Kato, S., Ito, S., Noguchi, T., and Naito, H. (1989) Biochim. Biophys. Acta 991, 36-43] and to cause a rapid and reversible dysfunction of cis- and trans-Golgi complexes (Fujiwara et al., supra; Lippincott-Schwartz, J. Yuan, L. C., Bonifacino, J. S. and Klausner, R. D. (1989) Cell 56, 801-813; Ulmer, J. B., and Palade, G. E. (1989) Proc. Natl. Acad. Sci. U.S.A. 86, 6992-6996; Ulmer, J. B., and Palade, G. E. (1991) J. Biol. Chem. 266, 9173-9179; Lippincott-Schwartz, J., Donaldson, J. G., Schweizer, A., Berger, E. G., Hauri, H., Yuan, L. C., and Klausner, R. D. (1990) Cell 60, 821-836]. BFA has also been shown to perturb the intracellular trafficking of endocytosed ricin and to inhibit ricin cytoxicity [Yoshida, T., Chen, C., Zhang, M., and Wu, H. C. (1991) Experimental Cell Research 192, 389-395). However, little is known about the effect of BFA on the transcellular trafficking of plasma membrane-associated proteins.

Pursuant to one preferred embodiment of the present invention, BFA is employed to markedly increase the receptor-mediated transcytosis of Tf and alter the intracellular trafficking of the TfR. Since the TfR exists in many types of epithelial and endothelial cells [Jefferies, W. A., Brandon, M. R., Hunt, S. V., Williams, A. F., Gatter, K. C., and Mason, D. Y. (1984) Nature 312, 162-163.; Banerjee, D., Flanagan, P. R., Cluett, J., and Valberg, L. S. (1986) Gastroenterol. 91, 861-869], including the endothelium of brain capillaries [Fishman, J. B., Rubin, J. B., Handrahan, J. V., Connor, J. R., and Fine, R. E. (1987) J. Neurosci. Res. 18, 299-304.; Pardridge, W. M., Eisenberg, J., and Yang, J. (1987) Metabolism 36, 892-895], this embodiment of the inventive method permits an increase in the transepithelial or transendothelial movement of receptor bound ligands or ligand-drug conjugates. In this regard, it is of interest to note that TfR has been considered to be a potential carrier for drug delivery across the blood-brain barrier [Pardridge, W. M., Triguero, D., and Buciak, J. I. (1990) Endocrinol. 126, 977-984]. It is, however, only through the use of the inventive combination of a cell-surface receptor ligand/active agent conjugate with a transcytosis accelerator (e.g., a conjugate of the active agent with Tf or TfR antibodies in combination with BFA) that acceptable rates of transcytosis are achieved; in the absence of an agent which accelerates transcytosis, unacceptably low delivery rates are achieved.

Conventional enhancers used to increase the passive diffusion of drug molecules suffer from a drawback of being nonspecific, i.e., once the perturbation of cell membrane occurs and cellular tight junctions have been disrupted by the enhancers, the increased permeability of the cell monolayer will not only allow the intended peptide/protein drug, but also other undesired compounds to pass across the monolayer. The absorption of these undesired compounds may cause toxicity and other side effects. BFA and monensin, however, have been found only to increase the transcytosis of Tf, and not EGF, asialoglycoproteins and fluid phase marker HRP, indicating that these enhancers are receptor-specific and that non-relevant substances will not be able to pass across the cells via the enhanced transcytotic pathway.

Most non-specific absorption enhancers act at a relatively high concentration and in a dose-dependent manner [Muranishi, S. (1990) Therapeutic Drug Carrier Systems 7, 1-33]. It has been reported that in order to achieve a 3.5-fold increase in the oral absorption of insulin from rat, the amount of salicylate as an enhancer at the site of absorption has to be 6 mg/rat or higher (up to 15 mg/rat, about a 5 mg/ml concentration) [Nishihata, T., Rytting, J. H., Kamada, A. and Higuchi, T. (1981) Diabetes 30, 1065]. According to the present invention, however, it has been determined that a 25- to 50-fold increase in TfR-mediated Tf transepithelial transport could be achieved with concentration of monensin or BFA of 4 $\mu$g/ml and 1.6 $\mu$g/ml, respectively, which is about 1000 times less in scale than that of conventional enhancers. While the following discussion focuses on the combination of TfR-ligand conjugate/BFA, it should of course be understood that the present invention is by no means limited to this particular combination of cell-surface receptor ligand conjugate and accelerator. For example, as noted supra, other types of cell-surface receptors are well known to undergo transcytosis with their associated ligands. For example, it is contemplated according to the present invention that the following cell-surface receptors may also be exploited by introducing the active agent in the form of a conjugate with the corresponding cell-surface receptor ligand: asialoglycoprotein receptors, low-density lipoprotein (LDL's) receptors and major histocompatibility complex (MHC) epitope receptors. Similarly, it is known in the art that enhancement (i.e., acceleration) of transcytosis of receptor/ligand complexes may be achieved with a variety of different agents, depending of course upon the particular receptor/ligand complex under consideration. Thus, in principle the present invention may employ as an enhancer of transcytosis an agent that influences or interferes with intracellular protein trafficking (e.g., within the endoplasmic reticulum, endosomes and/or Golgi apparatus) in a manner such that transcytosis of the receptor/ligand complex is enhanced. Accordingly, while a preferred embodiment is exemplified herein, the present invention provides a powerful technique for transmembrane and transcellular molecular transport of active agents which is limited only by the ability to identify an appropriate transport agent/accelerator combination targeted to the cell(s) of interest. In view of the differential distribution of particular receptors, moreover, the present invention provides the ability to selectively target cells or organs with great precision. As a consequence, it must be understood that following the teachings herein, it is now possible to overcome one of the primary obstacles to delivery of active agents (and in particular, peptides and proteins) in an essentially routine manner. As would of course be immediately apparent to those of skill in the art, formation of the ligand/active agent complex may be effected by a wide range of different techniques available to those working in the field; these techniques include not only covalent conjugate formation (e.g., the formation of a disulfide bridge between the active agent and the cell-surface receptor ligand), but also ionic and non-covalent conjugate complex formation (e.g., as exemplified by biotin/avidin complex formation, etc.). The choice of suitable technique for ligand/active agent conjugate formation may readily be made in an empirical manner, and would depend upon such obvious factors as the chemical nature of the ligand and the active agent, and the physicochemical and pharmacological properties of the conjugate (e.g., whether the conjugate per se have therapeutic utility or the active agent must be separated from the ligand for optimum therapeutic efficacy). Techniques for forming conjugates between active agents and suitable carriers are well known in the art of drug transport, and thus any suitable technique for forming a covalent, ionic or non-covalent conjugate between an active agent and a cell-surface receptor ligand as transport agent would be contemplated as within the scope of the present invention.

The invention may be better understood by reference to the following examples which are intended for purposes of illustration only and are not to be construed as in any way limiting the scope of the present invention, which is defined in the claims appended hereto.

EXAMPLES

Abbreviations used throughout are as follows: BFA, brefeldin A; EGF, epidermal growth factor; ER, endoplasmic reticulum; HA-MEM, Eagle's minimum essential medium with 0.1% of human albumin; PBS, phosphate-buffered saline, pH 7.4; TEER, transepithelial electrical resistance; Tf, transferrin; TfR, transferrin receptors.

EXAMPLE 1

Transcytosis of $^{125}$I-Tf and HRP in Filter-Grown MDCK Cells

Strain I MDCK cells were grown on 0.45-μm pore size polycarbonate filters in Transwells (Costar, Cambridge, Mass.) as has been described in the literature [Shen, W.-C., Wan, J., and Shen, D. (1990) *Biochem. Biophys. Res. Commun.* 166, 316–323]. Monolayers which displayed a transepithelial electrical resistance (TEER) of more than 2500 ohms cm$^2$ (as measured by an epithelial voltohmmeter, EVOM, World Precision Instruments, West Haven, Conn.) were used in experiments.

To remove endogenous Tf, MDCK cells used in all of the experiments were pre-treated as follows: confluent cell monolayers were rinsed 3 times with serum-free MEM, followed by incubation with serum-free MEM containing 1 mg/ml human albumin (fraction V, Sigma Chemical Co., St. Louis, Mo.) (HA-MEM) at 37° C. for 1 hr. After the incubation, the medium was replaced with fresh HA-MEM. The TEER of the cell monolayers was not changed by this pre-treatment.

Human apo-Tf (Sigma Chemical Co., St. Louis Mo.) was first loaded with iron [Larrick, J., and Cresswell, P. (1979) *Biochim. Biophys. Acta* 583, 483–490] and then labeled with $^{125}$I using the Iodo-Beads (Pierce Chemical Co. Rockford, Ill.) method as suggested by the supplier. Briefly, 0.7 mCi of Na$^{125}$I (ICN Radiochemicals, Irvine, Calif.) was incubated at 25° C. with 2 Iodo-beads for 5 in 0.22 ml of phosphate buffer (0.1M, pH 7.4), and then 20 μl of diferritransferrin (25 mg/ml) was added to the beads in the buffer solution. The solution was allowed to sit at 25° C. for 10 min and then any non-incorporated iodine was removed by filtration through a 20×0.5-cm Sephadex G-25 column (Pharmacia Fine Chemicals, Piscataway, N.J.). Apo-Tf was labeled with $^{59}$Fe by a previously reported method [Timchak, L. M., Kruse, F., Marnell, M. H., and Draper, R. K. (1986) *J. Biol. Chem.* 261. 14154–14159]. Eluted $^{59}$Fe-Tf and $^{125}$I-Tf fractions showed specific radioactivity levels of $10^4$ cpm/μg and $5\times10^5$ cpm/μg, respectively.

$^{125}$I-Tf (1.5 μg/ml), $^{59}$Fe-Tf (6 μg/ml), or HRP (3 μg/ml) was added with or without unlabeled Tf at a 200- to 300-fold molar excess to the apical (1.5 ml) or the basal (2.5 ml) medium of filter-grown MDCK cells and BFA (1.6 μg/ml) was added to the basal medium as well. At various time intervals, the basal or apical media containing transcytosed $^{125}$I-Tf or $^{59}$Fe-Tf was collected and an equal volume of fresh HA-MEM was added as replenishment. The $^{125}$I-Tf in the collected samples was subjected to 15% TCA precipitation and following centrifigation, the radioactivity in protein pellets was measured. For the media containing transported HRP, the HRP enzymatic activity was determined [Worthington Enzyme Mamual (1972) pp. 43–45, Worthington Biochem. Co., Freehold, N.J.]. After the last sample collection, cell monolayers were rinsed extensively with 4° C. serum-free MEM and then removed together with the filter membrane from the Transwell. The radioactivity level in the entire filter membrane containing $^{125}$I-Tf or $^{59}$Fe-Tf was counted in a Packard gamma counter.

Filter-grown MDCK cells were treated with BFA (1.6 μg/ml) in the basal medium at 37° C. for about 2 hours. After treatment, cells were rinsed extensively and the chambers were refilled with cold HA-MEM. $^{125}$I-Tf (1.5 μg/ml) with or without unlabeled Tf (350 μg/ml) was then added to either the apical or basal medium. Binding of $^{125}$I-Tf to the cells was measured at 4° C. for 3 hours. Following binding, the cells were rinsed extensively with cold HA-MEM and the cell-associated radioactivity was counted. The binding of $^{125}$I-Tf to the membranes in the presence of unlabeled Tf was treated as the non-specific binding of $^{125}$I-Tf to the membranes. The difference between the binding of $^{125}$I-Tf and $^{125}$I-Tf plus a large excess of unlabeled Tf to either the apical or the basal membrane of MDCK cells at 4° C. was considered to be the TfR-specific binding of $^{125}$I-Tf.

$^{125}$I-Tf (1.5 μg/ml) was added either with or without BFA (1.6 μg/ml) to the basal medium of filter-grown MDCK cells. Cells were incubated with the medium at 37° C. for 2 hr, after which the media was removed. Cells were then rinsed extensively with 4° C. serum-free medium to remove any unbound $^{125}$I-Tf. Cell-associated $^{125}$I-Tf, which included internalized and membrane-bound $^{125}$I-Tf, was chased at 37° C. in fresh HA-MEM medium or in the medium containing BFA (1.6 μg/ml). Both apical and basal medium were collected at various time intervals during the chase period, and the collected media was subjected to 15% TCA precipitation and the radioactivity in the TCA insoluble pellet was counted. $^{125}$I-Tf recovered from the basal medium was taken as a measure as of Tf recycling, while radioactivity appearing in the apical medium was used as a measure of Tf transcytosis.

Figure 1B:
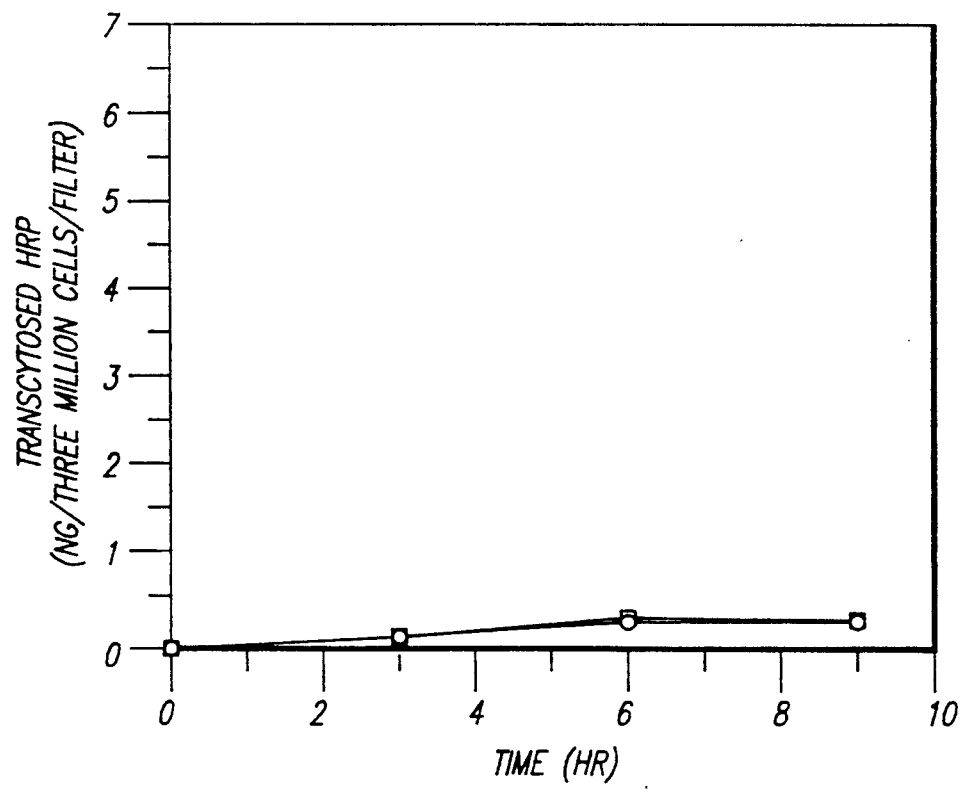

FIG. 1 illustrates transcytosis of $^{125}$I-Tf and HRP in filter-grown MDCK cells. $^{125}$I-Tf (1.5 μg/ml) either with or without unlabeled Tf (350 μg/ml) was added to the apical (AP) or basal (BL) medium of filter-grown MDCK cells. FIG. 1A shows the transcytosis of $^{125}$I-Tf in control cells (O □) and in BFA-treated cells (BFA:1.6 μg/ml) (● ■ in either the apical-to-basal (□ ■) or basal-to-apical (O ●) direction. When BFA was present in the basal medium, the transcytosis of $^{125}$I-labeled Tf ($^{125}$I-Tf) was markedly increased in both apical-to-basal and basal-to-apical directions (FIG. 1A), while the transcytosis of the fluid phase marker HRP remained unchanged (FIG. 1B). Briefly, cells were incubated with the medium at 37° C. for various time intervals and the BL or AP medium containing transcytosed $^{125}$I-Tf was collected. A constant volume of fresh medium was added to the cells and collected samples were subjected to 15% TCA precipitation. The radioactivity in the protein pellets after centrifugation was counted in a gamma counter and converted to the amount of protein using the specific radioactivity of $^{125}$I-Tf as $5 \times 10^5$ cpm/μg. Transcytosis of $^{125}$I-Tf in the presence of unlabeled Tf (non-specific transport) was less than 5% of that in the absence of unlabeled Tf (total transport). The difference between total and the non-specific transport is considered to be TfR-specific transport, as presented in the graph. FIG. 1B shows the transcytosis of HRP in BFA-treated and control cells. HRP (3 μg/ml) was added to either the apical or basal medium, and the HRP activity that appeared in the opposite medium to administration was measured using a HRP enzymatic assay. Each point represents the mean of triplicate cell monolayers with a standard deviation which is either indicated as a bar or is smaller than the size of the symbol. Each cell monolayer on the filter consisted of approximately $3 \times 10^6$ cells. The enhanced transcytosis of $^{125}$I-Tf was reduced by competition with excess unlabeled Tf.

Figure 2A:
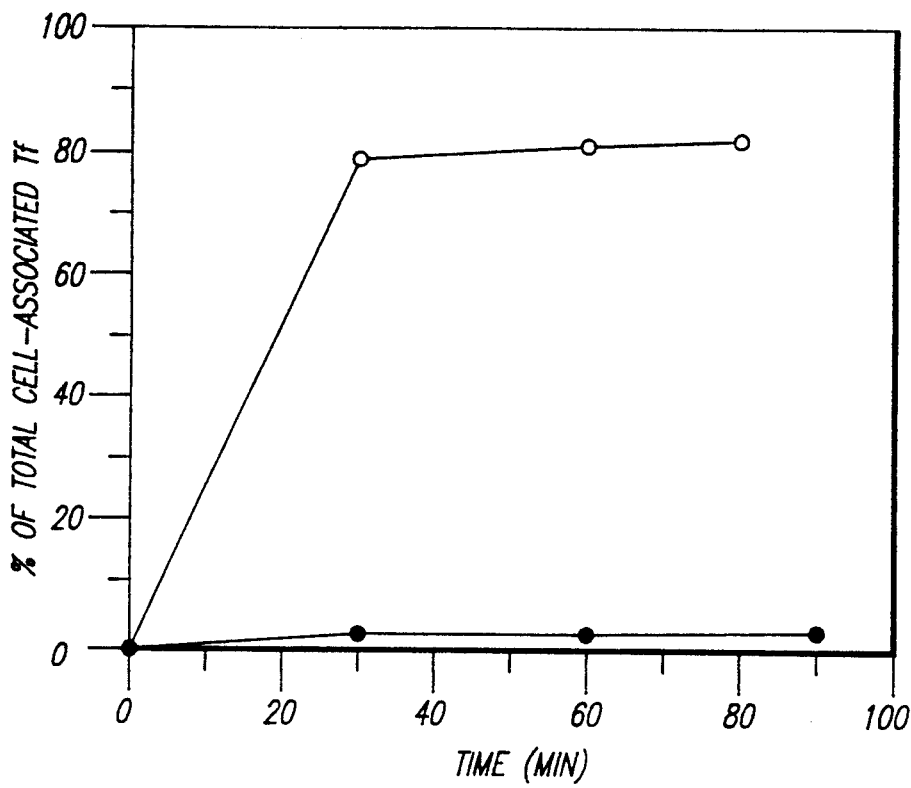
FIGS. 2A and 2B illustrate the results of pulse-chase experiments monitoring processing of cell-associated $^{125}$I-Tf with and without addition of bufeldin A (BFA), respectively.
Figure 2B:
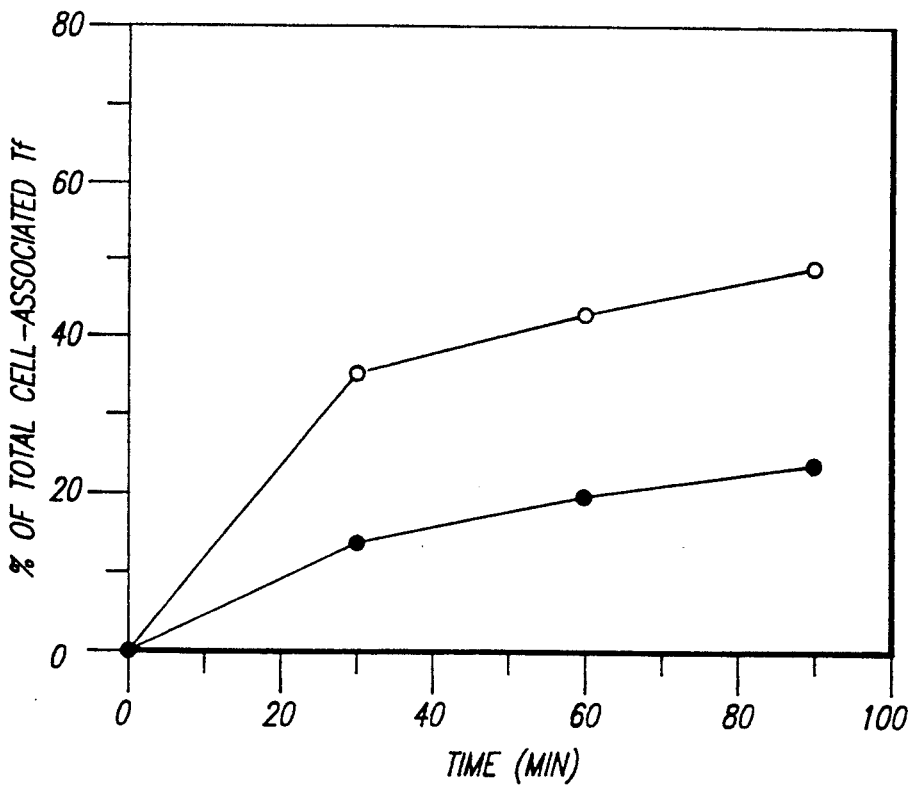

As further demonstrated by pulse-chase experiments, the intracellular processing of cell-associated $^{125}$I-Tf was profoundly altered by BFA. $^{125}$I-Tf (1.5 μg/ml) either with (FIG. 2B) or without (FIG. 2A) BFA (1.6 μg/ml) was added to the basal medium of filter-grown MDCK cells. Cells were incubated with the medium at 37° C. for 2 hours and then both apical and basal media were removed. Cells were then extensively rinsed with cold serum-free medium to remove unbound $^{125}$I-Tf. Cell-associated $^{125}$I-Tf (control cells: 19.2±0.2 ng/filter; BFA-treated cells: 22.6±0.3) was chased at 37° C. either in fresh HA-MEM medium or in the medium containing BFA (1.6 μg/ml). At different time intervals after the chase, both apical and basal medium were collected and subjected to 15% TCA precipitation. The radioactivity in the TCA-insoluble protein pellet was counted. $^{125}$I-Tf recovered from the basal medium was taken as recycled $^{125}$I-Tf (O), and $^{125}$I-If that was recovered from apical medium was taken as amount as trancytosed (●). Each point represents the mean of triplicate cell monolayers with a standard deviation which is either indicated as a bar or is smaller than the size of the symbol. Each cell monolayer on the filter consisted of approximately $3 \times 10^6$ cells. As is apparent from FIG. 2, 99% of internalized $^{125}$I-Tf was recycled to the basal medium and only 1% was transcytosed to the apical medium in control cells (FIG. 2A), but the ratio shifted to 70% recycling and 30% transcytosis in BFA-treated cells (FIG. 2B).

Figure 3:
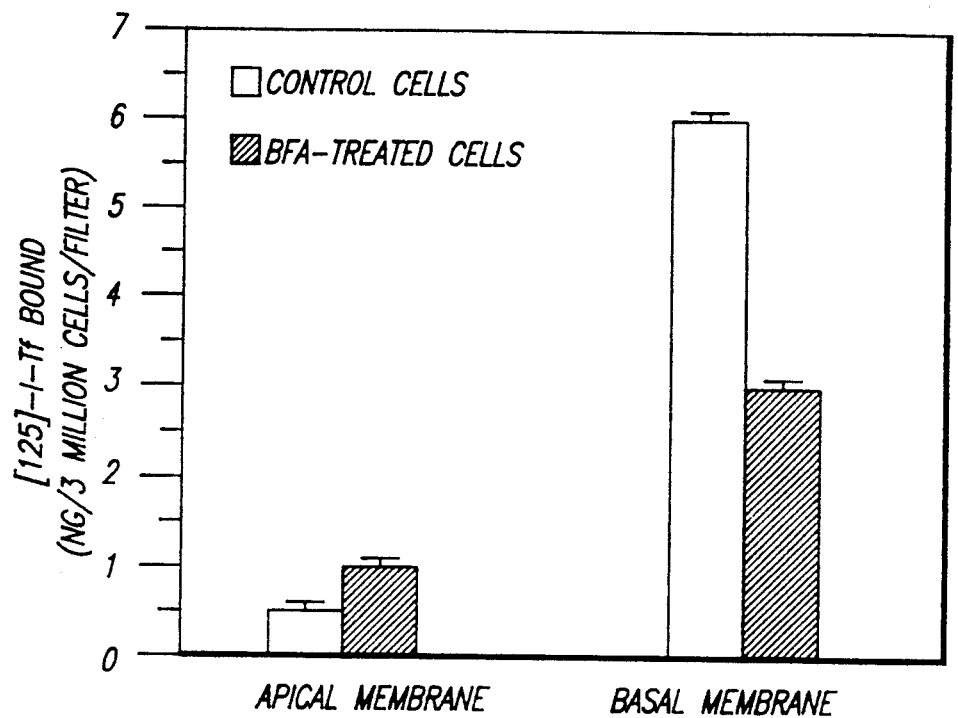
FIG. 3 illustrates changes in the specific binding of $^{125}$I-Tf to the basal and apical membranes upon treatment with BFA.

Exposure to BFA also led to a redistribution of TfR's, as demonstrated by the changes in the specific binding of $^{125}$I-Tf to the basal and apical membrane (FIG. 3). Filter-grown MDCK cells were treated (hatched column) or not treated (open column) with BFA (1.6 μg/ml) in the basal medium at 37° C. for 5 hr. After the treatment, both the apical and basal media were removed, and cells were rinsed extensively and then reincubated with HA-MEM at 4° C. $^{125}$I-Tf (1.5 μg/ml) was added either with or without unlabeled Tf (350 μg/ml) to the apical or basal medium. Binding of $^{125}$I-Tf to the cells was carried out at 4° C. for 3 hr. Following binding, both apical and basal medium were removed and cells were rinsed extensively with 4° C. HA-MEM to remove any unbound $^{125}$I-Tf. The cell-associated radioactivity was counted, and the difference between the total and non-specific binding (in presence of the unlabeled Tf) of $^{125}$I-Tf was taken as TfR-specific binding as presented in the graph. Each column represents the mean of triplicate cell monolayers with a standard deviation which is indicated as a bar or is smaller than the size of the symbol. Each cell monolayer on the filter consisted of approximately $3 \times 10^6$ cells. In control cells the amount of $^{125}$I-Tf specifically bound to the basal and apical membranes was 5.8 ng and 0.5 ng/$3 \times 10^6$ cells/filter, respectively. In BFA treated cells, these levels were shifted to 2.8 ng (basal) vs. 0.9 ng (apical) changing the ratio of basal to apical binding from 12:1 to 3:1.

Figure 4A:
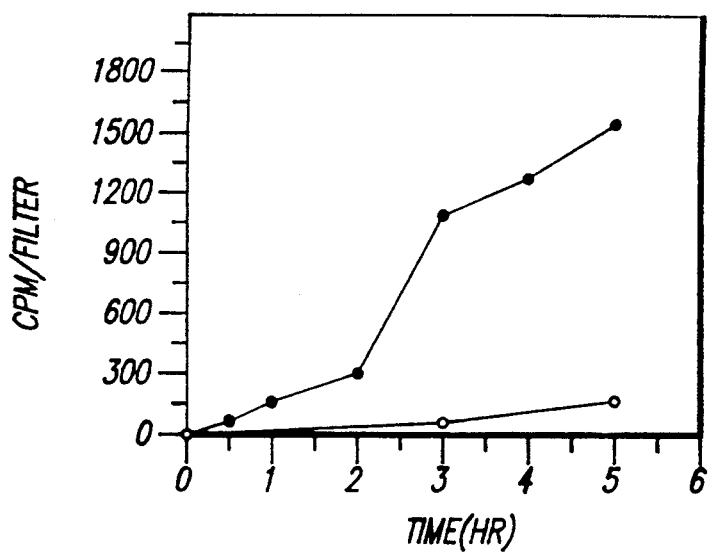
FIGS. 4A-4C illustrate the results of experiments to determine the effects of BFA on TfR-mediated uptake of $^{59}$Fe, FIG. 4A showing uptake from the apical membrane, 4B uptake from the basolateral membrane and 4C transcytosis in the basal-to-apical direction.
Figure 4B:
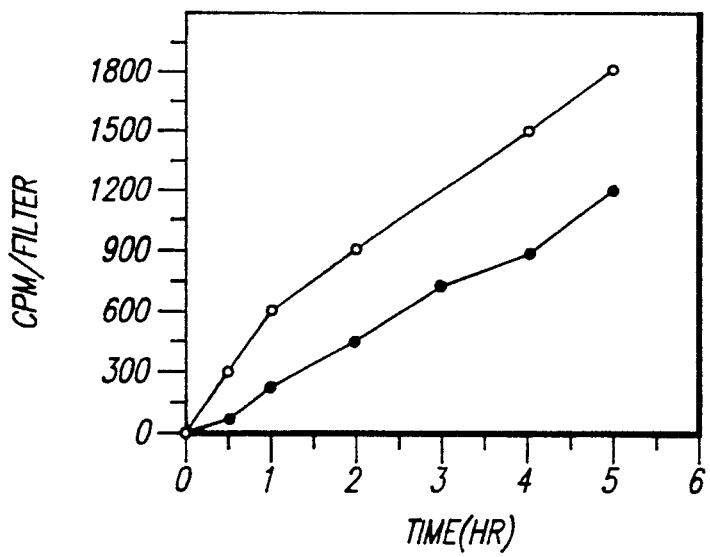
Figure 4C:
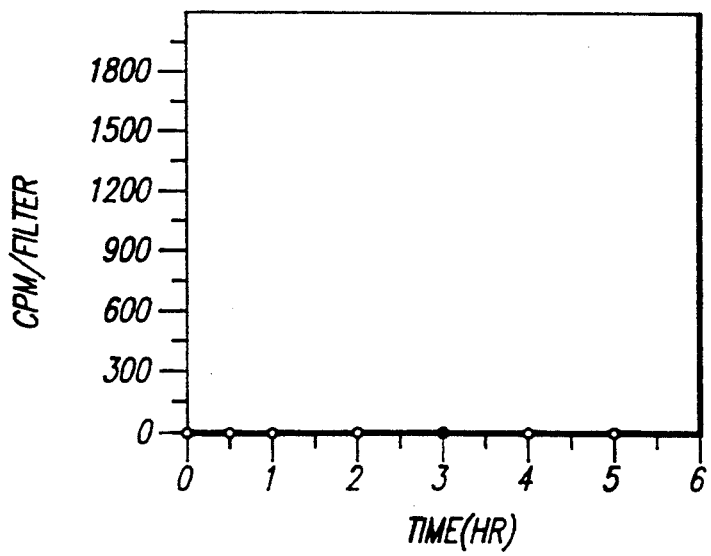

The effects of BFA on TfR-mediated uptake of $^{59}$Fe were also evaluated (FIG. 4). $^{59}$Fe-Tf (6 μg/ml) was added either with or without unlabeled Tf (1 mg/ml) to either the apical or basal medium of MDCK cells. Cells were either treated (●) or not treated with BFA (1.6 μg/ml) (O). After incubation at 37° C. for various time periods, the medium containing transcytosed Tf was collected and counted in a gamma counter. Cell monolayers were then rinsed extensively with cold medium to remove free $^{59}$Fe-Tf and then the cell associated-$^{59}$Fe was counted. Tf-mediated uptake of $^{59}$Fe, i.e., the difference between the total uptake and the uptake in presence of large excess of unlabeled Tf is presented in the graph. FIG. 4A shows Tf-mediated uptake of $^{59}$Fe from the apical membrane; FIG. 4B, safe uptake from the basolateral membrane; and FIG. 4C, $^{59}$Fe transcytosis in the basal-to-apical direction in control and BFA-treated cells. Transcytoses in the apical-to-basal direction in both cells were very similar to that in the basal-to-apical direction and are not presented. Ferric ions associated with Tf are efficiently extracted inside endosomes and accumulate in the cytosol following endocytosis [Klausner, R. D., van Renswoude, J. Kempf, C., Rao, K., Bateman, J. L., and Robbins, A. R. (1984) *J. Cell Biol*. 98, 1098–1101]. This process was not altered by BFA treatment, as indicated by the fact that $^{59}$Fe was not transcytosed in either control or BFA treated cells (FIG. 4C). Thus, $^{59}$Fe uptake can be used as an index of total Tf endocytosis occurring either from the basolateral or apical membranes. As was expected, very little endocytosis occurred from the apical surface of control cells (FIG. 4A). Surprisingly, BFA dramatically increased apical endocytosis and reduced endocytosis from the basal surface (FIG. 4A and B).

The extent of transcytosis of Tf from the basolateral to the apical surface in MDCK monolayers is very small, and apical-to-basal transcytosis is even less measurable (FIG. 1). This difference, as has also been shown by others [Fuller, S. D., and Simons, K. (1986) *J. Cell Biol.* 103, 1767–1779.; Lippincott-Schwartz, J. Yuan, L. C., Bonifacino, J. S. and Klausner, R.d. (1989) *Cell* 56, 801–813], reflects the fact that Tf receptors are predominantly localized on the basolateral membrane. Such asymmetries in receptor distribution have been documented in several instances [Simons, K., and Fuller, S. D. (1985) *Annu. Rev. Cell Biol.* 1, 243–288; Rodriguez-Boulan, E., and Nelson, W. J. (1989) *Science* 245, 718–725]. BFA markedly enhances Tf transcytosis in both apical-to-basal and basal-to-apical directions. This enhancement was not accompanied by a concurrent increase in the transcytosis of HRP, a fluid-phase marker, indicating that it was not caused by BFA-induced leakage or damage to the monolayer. Instead, this enhancement is specific to Tf receptor-mediated transport, as indicated by the fact that the transcytosis of $^{125}$I-Tf was decreased by the presence of excess unlabeled Tf. The transcytosis of ligands mediated by other receptors, such as EGF and asialoglycoprotein, was not affected by the same treatment.

The striking enhancement induced by BFA-treatment on Tf transcytosis must be due to a missorting of internalized Tf-TfR complexes, for several reasons: (1) the ratio of transcytosis vs. recycling of total cell-associated Tf was shifted from 1% vs. 99% in untreated cells to 30% vs. 70% in BFA-treated cells (FIG. 2A and 2B); (2) a two-fold increase in TfR levels was found in the apical membrane of BFA-treated cells (FIG. 3); and (3) a concomitant eight-fold increase in TfR-mediated $^{59}$Fe uptake from the apical membrane was also observed (FIG. 4A).

The difference between the increase in TfR level and the increase in TfR-mediated uptake of $^{59}$Fe from the apical membrane may imply that BFA only affects the intracellular routing of the Tf-TfR complex, but not the machinery which controls the polarity of cell membrane. It is likely that once the basolaterally internalized TfR is misdirected to the apical membrane it will be retrieved rapidly from the cell surface. Consequently, residence of the TfR on the apical membrane will be transient and the increase of TfR levels that can be detected at any given time point is significantly less than the increase of overall $^{59}$Fe uptake from the apical membrane. In contrast, the decrease in $^{59}$Fe uptake and TfR levels in the basal membrane in BFA-treated cells are 42% and 50%, respectively (FIG. 4B and FIG. 3). Thus, perhaps BFA only inhibits recycling but does not change the default location of the TfR on the basal membrane. The dynamic movement of the remaining TfR's on the basal membrane is not changed and therefore the level of $^{59}$Fe uptake is proportionally related to the level of TfR is present on the membrane.

It is known that BFA has no effect on endocytosis, endosome acidification, lysosomal function, or the trans-Golgi network [Misumi et al., supra; Yoshida et al., supra]. This is consistent with the finding reported herein that the cellular extraction of $^{59}$Fe from internalized $^{59}$Fe-Tf, presumably inside acidic endosomes, still normally occurs in BFA-treated cells (FIG. 4). Therefore, it is likely that BFA exerts its effect not by interfering with internalization, but rather by disrupting intracellular processing of the Tf-TfR complex. It has been shown that after internalization, a fraction of Tf-TfR passes through most, if not all, Golgi subcompartments [Fishman, J. B., and Fine, R. E. (1987) *Cell* 48, 157–164; Stein, B. S., and Sussman, H. H. (1986) *J. Biol. Chem.* 261, 10319–10331.; Woods et al., supra] and that post-translational modification of the Tf-TfR complex occurs in the Golgi apparatus [Regoeczi, E., Chindemi, P. A. and Debanne, M. T. (1984) *Can. J. Biochem. Cell Biol.* 62, 852–858; Snider et al., supra]. Perturbation of the Golgi cisternae by BFA may disrupt the processing of Tf-TfR and result in a missorting of the complex into a transcytotic pathway. On the other hand, BFA has been shown to curtail the vesicular transport of secretory proteins from the ER via cis- and trans-Golgi elements to the cell surface. Possibly, BFA effects the association of β-COP, a non-clathrin coating protein, to the Golgi membrane thus preventing the formation of non-clathrin coated vesicles budding from the cis-Golgi apparatus [Orci et al., supra]. Therefore, as an alternative mechanism, this inhibition of outwardly directed vesicular transport by BFA may indirectly affect the intracellular trafficking of incoming TfR containing endocytotic vesicles, presumably by decreasing the interaction between these two types of vesicles.

EXAMPLE 2

Transcytosis of HRP-SS-Tf in Filter-Grown MDCK Cells

For preparation of HRP-SS-Tf, 1.6 μmol of SPDP in 50 μl of ethanol was added slowly to 0.4 μmol of diferritransferrin in 0.64 ml PBS. In a separate reaction, 3.2 μmol of SPDP in 100 μl of ethanol was added to 0.8 μmol of HRP in 1 ml PBS, pH 7.5. Both reaction mixtures were gently stirred at 25° C. for 1 hour and then dialyzed overnight in 1 L PBS at 4° C. SPDP-modified HRP was reduced by 100 μl of 1M dithiothreitol (DTT) at 25° C. and then purified by Sephadex G-50 gel filtration. The purified sulfhydryl-containing HRP was added to SPDP-modified Tf and the reaction mixture was gently stirred for 3 hr at 25° C. and then overnight at 4° C. The unconjugated HRP and Tf were removed by Sephadex G-100 gel filtration. Fractions containing TF-SS-HRP conjugate were identified by HRP activity measurement and analyzed by SDS-polyacrylamide gel electrophoresis (SDS-Page) with a 7.5% gel. After staining with coomassie Blue, the conjugate showed as a major band in SDS-PAGE with an apparent molecular mass of 120 kDa. This major band disappeared when DTT was added to the conjugate before the electrophoresis, confirming that HRP and Tf were linked by a disulfide linkage. The molar ratio of HRP to Tf in the conjugate was 1.29:1 as estimated by the measurement of absorbance at 403 nm for HRP and 280 nm for the total protein.

Transport of the HRP covalently coupled to Tf via a disulfide linkage (HRP-SS-Tf) across epithelial cells in presence of monensin, NH$_4$Cl and BFA was measured. Transcytosis of TF-SS-HRP was monitored by HRP enzymatic activity. HRP enzymatic activity was determined by the literature method [Worthington Enzyme Manual (1972), Worthington Biochem. Co., Freehold, N.J., pp. 43–45].

FIG. 5 illustrates the effects of monensin and NH$_4$Cl on the transcytosis of HRP-SS-Tf (FIG. 5A) and HRP (FIG. 5B) in filter-grown MDCK cells. HRP-SS-Tf (3 μg HRP/ml) and HRP (3 μg/ml), alone or together with either unlabeled Tf (1 mg/ml), monensin (6 μM) or NH$_4$Cl (20 mM), was added to the basal medium. After incubation at 37° C. for various time periods, the HRP enzymatic activity appearing in the apical medium was measured. The data is presented as the mean ±S.D., n=3. FIG. 5A shows that the transcytosis of control Tf-SS-HRP in the basal-to-apical direction occurred at a very low rate of 0.05 ng/filter/hours, which is expected because it was shown that $^{125}$I-Tf transcytosis was very low. However, the presence of monensin (6 μM) increased the transcytosis of TF-SS-HRP by about 9-fold. This enhanced transcytosis was TfR-mediated because the addition of a large excess of unconjugated Tf reduced the transcytosis by about 90%. The presence of NH$_4$Cl (20 mM) increased the transcytosis of TF-SS-HRP by about 2-fold. FIG. 5B shows that the presence of monensin only increased the transcytosis of HRP-SS-Tf, but not that of free HRP, indicating that the enhanced transcytosis is not due to the drug-induced increase of cellular permeability.

FIG. 6 shows the effects of BFA on the transcytosis of HRP-SS-Tf (FIG. 6A) and HRP (FIG. 6B) in filter-grown MDCK cells. HRP-SS-Tf (3 μg HRP/ml) and HRP (3 μg/ml), alone or together with either unlabeled Tf (1 mg/ml) and BFA (1.6 μg/ml), was added to the apical medium. After incubation at 37° C. for various time periods, the HRP enzymatic activity in the basal medium was measured. Again, the data is presented as the mean ±S.D., n=3. FIG. 6A shows that presence of BFA increased the transcytosis of HRP-SS-TF in the apical-to-basal direction in MDCK cells by about 25-fold. This enhanced transcytosis was reduced by more than 90% upon addition of unconjugated free Tf, indicating that it was due to a receptor-mediated mechanism. FIG. 6B shows that the presence of BFA does not affect the transcytosis of free HRP.

Figure 7:
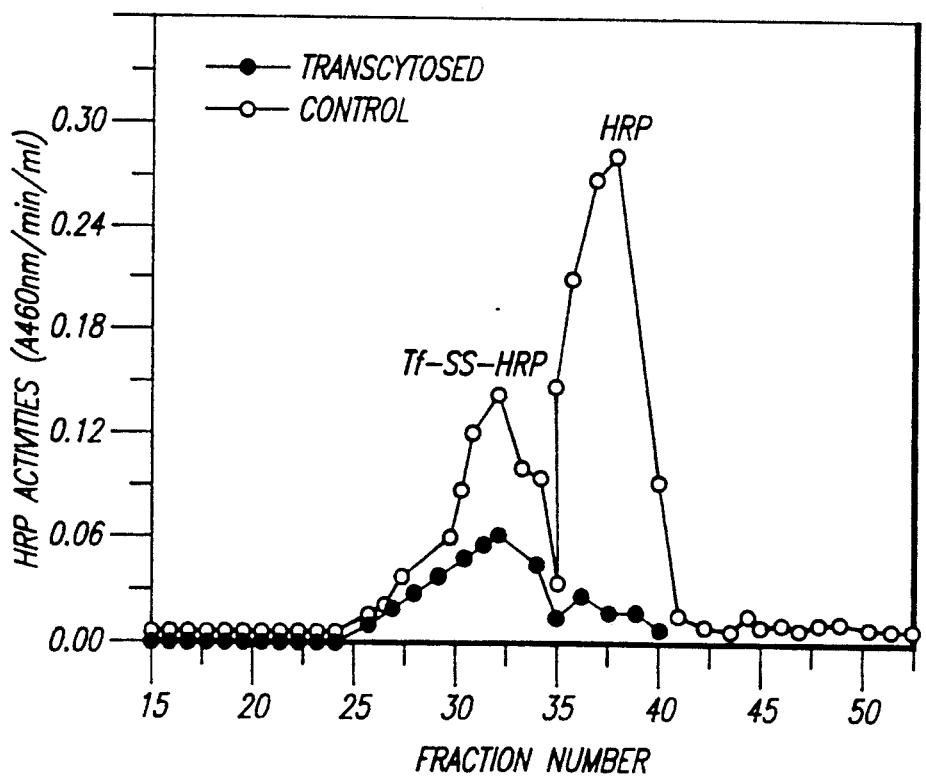
FIG. 7 illustrates the elution pattern of transcytosed TF-SS-HRP and a control standard in Sephacryl S-200 gel chromatography.

The integrity of transcytosed TF-SS-HRP was demonstrated by retention of HRP enzymatic activity as indicated in FIGS. 5 and 6, and also by Sephacryl S-200 gel chromatography (FIG. 7). The medium containing transcytosed HRP-SS-Tf was concentrated using a Centricon-10 filter unit, and was then loaded onto the Sephacryl S-200 column (1.5×70 cm). Fractions containing HRP activity were determined. The resultant elution profile was compared with that of the standard Tf-SS-HRP and HRP from the same column. The transcytosed TF-SS-HRP was eluted off from the column at fractions which coincided with those of intact Tf-SS-HRP.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A method for enhancing transcellular or transmembrane transport of an active agent, said method comprising:
    forming a conjugate of said active agent with a cell-surface receptor ligand for a transferrin receptor; and
    administering said conjugate and a transfer enhancing amount of a transfer enhancement agent which enhances transcytosis of a cell-surface receptor/ligand complex.

2. A method according to claim 1, wherein said transfer enhancement agent is brefeldin A or monensin.

* * * * *

UNITED STATES PATENT AND TRADEMARK OFFICE
CERTIFICATE OF CORRECTION

PATENT NO. : 5,254,342

DATED : October 19, 1993

INVENTOR(S) : Shen, Wei-Chiang and Wan, Jiansheng

It is certified that error appears in the above-indentified patent and that said Letters Patent is hereby corrected as shown below:

| Column | Line | |
|---|---|---|
| 18 | 11 | After "5", insert --min.--. |
| 18 | 21 | Replace "261." with --261,--. |

Signed and Sealed this

Twenty-sixth Day of April, 1994

Attest:

BRUCE LEHMAN

*Attesting Officer*       *Commissioner of Patents and Trademarks*